United States Patent
Umemoto et al.

(10) Patent No.: US 7,381,846 B2
(45) Date of Patent: Jun. 3, 2008

(54) SUBSTITUTED PHENYLSULFUR TRIFLUORIDE AND OTHER LIKE FLUORINATING AGENTS

(75) Inventors: Teruo Umemoto, Denver, CO (US); Rajendra P. Singh, Broomfield, CO (US)

(73) Assignee: IM&T Research, Inc., Denver, CO (US)

( * ) Notice: Subject to any disclaimer, the term of this patent is extended or adjusted under 35 U.S.C. 154(b) by 0 days.

(21) Appl. No.: 11/828,162

(22) Filed: Jul. 25, 2007

(65) Prior Publication Data

US 2008/0039660 A1    Feb. 14, 2008

Related U.S. Application Data

(63) Continuation-in-part of application No. 11/494,983, filed on Jul. 28, 2006, now Pat. No. 7,265,247.

(51) Int. Cl.
*C07C 321/00* (2006.01)
*C07C 323/00* (2006.01)
*C07C 381/00* (2006.01)

(52) U.S. Cl. .......................................... 568/23; 568/18
(58) Field of Classification Search ................ 568/23, 568/18
See application file for complete search history.

(56) References Cited

U.S. PATENT DOCUMENTS 6,222,064 B1    4/2001  Lal et al.
7,087,681 B2    8/2006  Umemoto
7,265,247 B1 *  9/2007  Umemoto et al. ............ 568/23
2005/0012072 A1  1/2005  Bailey et al.

FOREIGN PATENT DOCUMENTS

JP    P2000-38370 A    7/1990

OTHER PUBLICATIONS

Ou et al., Oxidative fluorination of S, Se and Te compounds, Journal of Fluorine Chemistry (2000), 101(2), 279-283.*
Calmari (1979) C&EN Letters Mar. 19 p. 4.
Kobayashi (2004) Tetrahedron 60 p. 6923.
Lal (1999) Chem. Commun. p. 215.
Middleton (1974) J. Org. Chem. 40 p. 574.
Olah (1973) J. Ameri. Chem. Soc. 96 p. 925.
Pashinnik (2003) Synthetic Communications 33 p. 2505.
Sheppard (1962) J. Chem. Soc. 84 p. 3058.
Sheppard (1972) J. Fluorine Chem. 2 p. 53.
Tullock (1960) Monaish. Chem. 88 p. 539.
Unknown (1981) Acta Chimica Sinica 39 p. 64.

* cited by examiner

*Primary Examiner*—Yvonne (Bonnie) Eyler
*Assistant Examiner*—Chukwuma O. Nwanonicha
(74) *Attorney, Agent, or Firm*—Swanson & Bratschun, L.L.C.

(57) ABSTRACT

Novel substituted phenylsulfur trifluorides that act as fluorinating agents are disclosed. Also disclosed are methods for their preparation and methods for their use in introducing one or more fluorine atoms into target substrate compounds. Finally, various intermediate compounds for use in preparing substituted phenylsulfur trifluorides are provided.

39 Claims, No Drawings

SUBSTITUTED PHENYLSULFUR TRIFLUORIDE AND OTHER LIKE FLUORINATING AGENTS

RELATED APPLICATION

This application claims priority to U.S. patent application Ser. No. 11/494,983 entitled "Substituted Phenylsulfur Trifluoride and Other Like Fluorinating Agents," filed Jul. 28, 2006 now U.S. Pat. No. 7,265,247, the disclosure of which is hereby incorporated by reference in its entirety.

TECHNICAL FIELD

The present invention relates to fluorinating agents and more particularly to novel substituted phenylsulfur trifluorides that act as fluorinating agents.

BACKGROUND OF THE INVENTION

Fluorine-containing compounds have found wide use in medical, agricultural, electronic materials and other like industries (see Chemical & Engineering News, June 5, pp 15-32 (2006); Angew. Chem. Ind. Ed., Vol. 39, pp 4216-4235 (2000)). These compounds show specific biologic activity or physical properties based on the presence of one or more fluorine atoms. A particular drawback in their usefulness is the scarcity of natural fluorine-containing compounds, requiring most such compounds to be prepared through organic synthesis.

Fluorinating agents are compounds that selectively introduce fluorine atom(s) into target compounds through one or more chemical reactions to produce fluorine-containing compounds. Particularly useful fluorinating agents have the capacity to replace oxygen or oxygen-containing groups in the target compound with fluorine. A number of fluorinating agents have been discovered; however, as discussed in more detail below, all of these agents have significant drawbacks based on safety, reactivity, storage stability, and/or disposability.

Illustrative examples of known fluorinating agents include: sulfur tetrafluoride ($SF_4$), a highly toxic gas that is often utilized under pressure [J. Am. Chem. Soc., Vol. 82, pp 543-551 (1960)]; N,N-diethylaminosulfur trifluoride (DAST), an unstable liquid agent having a highly explosive nature, i.e., low thermal stability and large amounts of thermal energy upon decomposition [J. Org. Chem., Vol. 40, pp 574-578 (1975) and Chem. & Eng. News, Vol. 57, No. 19, p 4 (1979)]; bis(methoxyethyl)aminosulfur trifluoride (Deoxo-Fluor®) a product having greater thermal stability than DAST but still having a starting decomposition temperature similar to DAST [Chemical Communications, pp 215-216 (1999)]; selenium tetrafluoride ($SeF_4$), a highly toxic selenium compound [J. Am. Chem. Soc., Vol. 96, pp 925-927 (1974)]; and various other more designed fluorinating agents that provide greater safety but have provided substantially reduced reactivity and yields: phenylfluorophosphane reagents [$Ph_nPF_{5-n}$ (n=1~3), Chem. Pharm. Bull., Vol. 16, p 10009 (1968)], α,α-difluoroalkylamino reagents [$ClCFHCF_2NEt_2$, Organic Reactions, Vol. 21, pp 158-173 (1974); $CF_3CFHCF_2NEt_2$, Bull. Chem. Soc. Jpn, Vol. 52, pp 3377-3380 (1979); $CF_2HCF_2NMe_2$, J. Fluorine Chem., Vol. 109, pp 25-31 (2001)], 2,2-difluoro-1,3-dimethylimidazolidine [Jpn. Kokai Tokyo Koho JP 2000 38, 370; Chemical Communications, pp 1618-1619 (2002)], and [(m-methylphenyl)difluoromethyl]diethylamine (Tetrahedron, Vol. 60, pp 6923-6930).

In addition, phenylsulfur trifluoride has also been synthesized and used as a fluorinating agent, but its fluorination yields have proven low and its applicability is narrow [J. Am. Chem. Soc., Vol. 84, pp 3058-3063 (1962); Acta Chimica Sinica, Vol. 39, No. 1, pp 63-68 (1981); and see Comparison Example 1 in Table 5]. Pentafluorophenylsulfur trifluoride was also synthesized and used as a fluorinating agent, but has proven costly, since its starting material is expensive and it has only two reactive fluorine atoms out of eight existing in the molecule [J. Fluorine Chem., Vol. 2, pp 53-62 (1972/73)]. More recently, p-nitrophenylsulfur trifluoride was examined and also shown to have little or no fluorination ability [Acta Chimica Sinica, Vol. 39, No. 1, pp 63-68 (1981)].

Each of these conventional illustrative fluorinating agents requires room for improvement on providing more effective and safer reagents for use in the production of these important fluorine-containing compounds.

As such, there is a need in the field to provide safe, reactive, less hazardous, cost effective, fluorinating agents, especially fluorinating agents that selectively introduce fluorine atoms into compounds by replacement of oxygen or oxygen-containing groups with fluorine atoms. Ideally, these fluorinating agents provide high yields and can be handled and stored in a safe manner.

The present invention is directed toward overcoming one or more of the problems discussed above.

SUMMARY OF THE INVENTION

The present invention provides novel fluorinating agents for use in the introduction of fluorine atoms into target compounds. The resultant target compounds, i.e., fluorine-containing compounds, have been shown to have tremendous potential in medical, agricultural, electronic materials' and other like uses.

In general, fluorinating agents of the invention are novel substituted phenylsulfur trifluoride compounds. The substituted phenylsulfur trifluoride compounds are shown herein to have substantial functional and safety benefits over conventional fluorinating agents.

The present invention also provides new intermediate compounds for use in the synthesis of the novel substituted phenylsulfur trifluorides.

Finally, the present invention provides synthesis schemes for the novel compounds of the invention, and data illustrating the use of these agents in preparing various fluorine-containing compounds.

DETAILED DESCRIPTION OF THE INVENTION

The present invention provides novel fluorinating agents for use in introducing fluorine atoms into target compounds. In the present invention the term "target compound" includes any substrate that once fluorinated is useful in the medical, agricultural, biological, electronic materials' or other like field, i.e., is a fluorine-containing compound. In preferred instances, the target compound(s) of the invention include one or more oxygen atom(s) and/or one or more oxygen-containing group(s), and/or one or more sulfur atom(s) and/or one or more sulfur-containing group(s) for selective replacement by the fluorine atom(s). Illustrative target compounds include alcohols, aldehydes, ketones, carboxylic acids, acid halides, esters, acid anhydrides, amides, imides, epoxides, lactones, lactams, sulfonic acids, sulfinic acids, sulfenic acids, thiols, sulfides, sulfoxides, thioketones, thioesters, dithioesters, thiocarboxylic acids, dithiocarboxylic acids, thiocarbonates, dithiocarbonates, trithiocarbonates, thioketals, dithioketals, thioacetals, dithioacetals, thioamides, thiocarbamates, dithiocarbamates, orthothioesters, phosphines, phosphine oxides, phosphine sulfides, and phosphonic acids.

Embodiments of the invention include novel substituted phenylsulfur trifluorides. Novel substituted phenylsulfur trifluorides are shown herein to be potent agents for selectively introducing fluorine atoms into target compounds thereby producing fluorine-containing compounds.

Fluorinating agents of the present invention show high thermal stability, having high decomposition temperatures and low exothermic heat ($-\Delta H$) values as compared to the conventional useful agents, DAST and Deoxy-Fluor® (see Examples below). In addition, fluorinating agents of the invention are highly reactive with a number of different target compounds, typically providing high yields of fluorine-containing product compounds. Although the known compounds, phenylsulfur trifluoride ($PhSF_3$) and p-methylphenylsulfur trifluoride (p-$CH_3C_6H_4SF_3$) (J. Am. Chem. Soc., Vol. 84, pp 3058-3063 (1962)) have high decomposition temperatures, they have high exothermic heat and their fluorination reactivity is low (see Examples below). The high stability and reactivity of the present invention's compounds is unexpected when compared to those of conventional fluorinating agents, i.e., DAST, Deoxo-Fluor®, $PhSF_3$, and the like.

Embodiments of the invention also provide methods for preparing the fluorinating agents and for using the fluorinating agents in the preparation of fluorine-containing compounds.

The invention provides compounds of the formula (I):

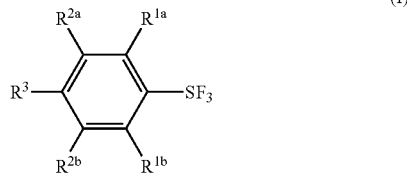

(I)

in which $R^{1a}$ and $R^{1b}$ can independently be a hydrogen atom; a primary or secondary alkyl group having from one to eight carbon atoms; or a primary, secondary, or tertiary alkyl group having one to eight carbon atoms and at least one ether linkage;

$R^{2a}$, $R^{2b}$, and $R^3$ are independently a hydrogen atom; a halogen atom; a primary, secondary, or tertiary alkyl group having from one to eight carbon atoms; or a primary, secondary, or tertiary alkyl group having one to eight carbon atoms and at least one ether linkage;

provided that, when $R^3$ is a hydrogen atom, at least two of $R^{1a}$, $R^{1b}$, $R^{2a}$, and $R^{2b}$ each is independently a halogen atom; a primary, secondary, or tertiary alkyl group having from one to eight carbon atoms; or a primary, secondary, or tertiary alkyl group having two to eight carbon atoms and at least one ether linkage; or, at least one of $R^{1a}$, $R^{1b}$, $R^{2a}$, and $R^{2b}$ is a primary, secondary, or tertiary alkyl group having two to eight carbon atoms and at least one ether linkage.

Further, when $R^3$ is a primary alkyl group having one to eight carbon atoms, at least one of $R^{1a}$, $R^{1b}$, $R^{2a}$, and $R^{2b}$ is a halogen atom; a primary, secondary, or tertiary alkyl group having from one to eight carbon atoms; or a primary, secondary, or tertiary alkyl group having two to eight carbon atoms and at least one ether linkage; and when at least two of $R^{2a}$, $R^{2b}$, and $R^3$ are tertiary alkyl groups, the tertiary alkyl groups are non-adjacent.

In preferred embodiments of formula (I), the alkyl groups have from one to four carbon atoms, and the alkyl groups having an ether linkage(s) have from two to five carbon atoms. More preferred alkyl groups of $R^3$ are tertiary alkyl groups, and most preferred alkyl group of $R^3$ is tert-butyl group.

Some embodiments of the invention are those compounds of formula (I) where primary or secondary alkyl groups of $R^{1a}$ and $R^{1b}$ having from one to eight carbon atoms, include: primary alkyl groups such as $CH_3$, $CH_2CH_3$, $CH_2(CH_2)_nCH_3$ (n=1-6), $CH_2CH(CH_3)_2$, and $CH_2C(CH_3)_3$, and secondary alkyl groups such as $CH(CH_3)_2$, $CH(CH_3)CH_2CH_3$, and $CH(CH_3)CH_2(CH_2)_nCH_3$ (n=1-4). More preferred primary or secondary alkyl groups of $R^{1a}$ and $R^{1b}$ include: $CH_3$, $CH_2CH_3$, $CH_2(CH_2)_nCH_3$ (n=1 or 2), $CH_2CH(CH_3)CH_3$, and $CH(CH_3)_2$, and, most preferred primary or secondary alkyl groups are $CH_3$ and $CH(CH_3)_2$.

Other embodiments of the invention are those fluorinating agents where primary, secondary, or tertiary alkyl groups having from one to eight carbon atoms of $R^{2a}$ and $R^{2b}$ include: primary alkyl groups such as $CH_3$, $CH_2CH_3$, $CH_2(CH_2)_nCH_3$ (n=1-6), $CH_2CH(CH_3)_2$, and $CH_2C(CH_3)_3$, secondary alkyl groups such as $CH(CH_3)_2$, $CH(CH_3)CH_2CH_3$, $CH(CH_3)CH_2(CH_2)_nCH_3$ (n=1-4), and tertiary alkyl groups such as $C(CH_3)_3$, $C(CH_3)_2CH_2CH_3$, and $C(CH_3)_2CH_2(CH_2)_nCH_3$ (n=1-3). More preferred primary, secondary, or tertiary alkyl groups having from one to eight carbon atoms of $R^{2a}$ and $R^{2b}$ include: $CH_3$, $CH_2CH_3$, $CH_2(CH_2)_nCH_3$ (n=1, 2), $CH_2CH(CH_3)_2$, $CH(CH_3)_2$, $CH(CH_3)CH_2CH_3$, and $C(CH_3)_3$, and most preferred primary, secondary, or tertiary alkyl groups are $CH_3$, $CH(CH_3)_2$, and $C(CH_3)_3$.

Other embodiments of the invention are those fluorinating agents where primary, secondary, or tertiary alkyl groups of $R^3$ having from one to eight carbon atoms, include: primary alkyl groups such as $CH_3$, $CH_2CH_3$, $CH_2(CH_2)_nCH_3$ (n=1-6), $CH_2CH(CH_3)_2$, and $CH_2C(CH_3)_3$, secondary alkyl groups such as $CH(CH_3)_2$, $CH(CH_3)CH_2CH_3$, $CH(CH_3)CH_2(CH_2)_nCH_3$ (n=1-4), and tertiary alkyl groups such as $C(CH_3)_3$, $C(CH_3)_2CH_2CH_3$, and $C(CH_3)_2CH_2(CH_2)_nCH_3$ (n=1-3). More preferred primary, secondary, or tertiary alkyl groups of $R^3$ having from one to eight carbon atoms include: $CH_3$, $CH_2CH_3$, $CH_2(CH_2)_nCH_3$ (n=1, 2), $CH_2CH(CH_3)_2$, $CH(CH_3)_2$, $CH(CH_3)CH_2CH_3$, and $C(CH_3)_3$, and most preferred primary, secondary, or tertiary groups of $R^3$ are $CH_3$, $CH(CH_3)_2$, and $C(CH_3)_3$.

Some embodiments of the invention are those compounds of formula (I) where primary, secondary, or tertiary alkyl groups of $R^{1a}$, $R^{1b}$, $R^{2a}$, $R^{2b}$, and $R^3$ having from two to eight carbon atoms and at least one ether linkage include: primary alkyl groups such as $CH_2OCH_3$, $CH_2OCH_2CH_3$, $CH_2OCH_2(CH_2)_nCH_3$ (n=1-5), $CH_2OCH(CH_3)_2$, $CH_2OCH(CH_3)CH_2CH_3$, $CH_2OCH_2CH(CH_3)_2$, $CH_2OC(CH_3)_3$, $CH_2CH_2OCH_3$, $CH_2CH_2OCH_2CH_2OCH_3$, $CH_2O(CH_2CH_2O)_nCH_2CH_3$ (n=1, 2), $CH_2O(CH_2CH_2O)_nCH_3$ (n=1-3), $CH_2O(CH_2CH_2CH_2O)_nCH_3$ (n=1, 2), $CH_2O[CH(CH_3)CH_2O]_nCH_3$ (n=1, 2), and $CH_2O[CH_2CH(CH_3)O]_nCH_3$ (n=1, 2); secondary alkyl groups such as $CH(CH_3)OCH_3$, $CH(CH_3)OCH_2CH_3$, and $CH(CH_3)CH_2OCH_3$; and tertiary alkyl groups such as $C(CH_3)_2OCH_3$, $C(CH_3)_2OCH_2CH_3$, and $C(CH_3)_2CH_2OCH_3$. More preferred primary, secondary or tertiary alkyl groups of $R^{1a}$, $R^{1b}$, $R^{2a}$, $R^{2b}$, and $R^3$ having at least one ether linkage include:

$CH_2OCH_3$, $CH_2OCH_2CH_3$, $CH_2OCH_2CH_2CH_3$, $CH_2OCH(CH_3)_2$, $CH_2OCH_2(CH_2)_2CH_3$, $CH_2OCH(CH_3)CH_2CH_3$, $CH_2OCH_2CH(CH_3)_2$, $CH_2OC(CH_3)_3$, $CH_2OCH_2C(CH_3)_3$, $CH_2OCH_2CH_2OCH_3$, $CH_2OCH_2CH_2OCH_2CH_3$, $CH_2OCH_2CH_2OCH_3$, $CH_2CH_2OCH_3$, $CH_2CH_2OCH_2CH_3$, $CH_2CH_2OCH(CH_3)_2$, $CH_2CH_2OCH_2CH_2OCH_3$, $CH(CH_3)OCH_3$, $CH(CH_3)OCH_2CH_3$, $C(CH_3)_2OCH_3$, and $C(CH_3)_2OCH_2CH_3$, and the most preferred alkyl groups having at least one ether linkage are $CH_2OCH_3$, $CH_2OCH_2CH_3$, $CH_2OCH(CH_3)_2$, and $CH_2OCH_2CH(CH_3)_2$.

When used herein, the term "halogen atom" or "halo" include fluorine, chlorine, bromine and iodine and fluoro, chloro, bromo, and iodo, respectively.

Examples of preferred halogen atoms of $R^{2a}$, $R^{2b}$, and $R^3$ include: fluorine, chlorine, bromine or iodine atoms, among these halogen types, fluorine, chlorine or bromine are more preferred, fluorine and chlorine are furthermore preferred, and chlorine is most preferred.

When used herein, the term "alkyl" includes all straight and branched isomers. Representative examples of alkyl groups include methyl, ethyl, propyl, isopropyl, butyl, isobutyl, sec-butyl, tert-butyl, pentyl, isopentyl, neopentyl, tert-pentyl, hexyl, heptyl, and octyl. Alkyl may include an alkyl substituted with a chlorine atoms(s) and/or a fluorine atom(s) such as $CH_2Cl$ and $CH_2F$.

When used herein, the term "ether linkage" is carbon atom-oxygen atom-carbon atom bonding (C—O—C).

Table 1 provides illustrative combinations of $R^{1a}$, $R^{1b}$, $R^{2a}$, $R^{2b}$ and $R^3$ for inclusion in formula (I).

TABLE 1

Illustrative Examples of Substituted Phenylsulfur Trifluoride Compounds of Formula (I) Showing $R^{1a}$, $R^{1b}$, $R^{2a}$, $R^{2b}$, and $R^3$ Combinations Based On Substitutions Into Formula (I)

| $R^{1a}$ | $R^{1b}$ | $R^{2a}$ | $R^{2b}$ | $R^3$ |
|---|---|---|---|---|
| H | H | H | H | $C(CH_3)_3$ |
| H | H | H | H | $C(CH_3)_2CH_2CH_3$ |
| H | H | H | H | $C(CH_3)_2(CH_2)_2CH_3$ |
| H | H | H | H | $C(CH_3)_2(CH_2)_3CH_3$ |
| H | H | H | H | $C(CH_3)_2(CH_2)_4CH_3$ |
| H | H | $C(CH_3)_3$ | $C(CH_3)_3$ | H |
| $CH_3$ | H | H | H | $C(CH_3)_3$ |
| $CH_3$ | $CH_3$ | H | H | $C(CH_3)_3$ |
| $CH_3$ | $CH_3$ | H | H | $CH(CH_3)CH_2CH_3$ |
| $CH_3$ | $CH_3$ | H | H | $CH_2CH(CH_3)_2$ |
| $CH_3$ | $CH_3$ | H | H | $CH_2(CH_3)_2CH_3$ |
| $CH_3$ | $CH_3$ | H | H | $CH_2CH_2CH_3$ |
| $CH_3$ | $CH_3$ | H | H | $C_2H_5$ |
| $C_2H_5$ | $C_2H_5$ | H | H | $C(CH_3)_3$ |
| $CH_2CH_2CH_3$ | $CH_2CH_2CH_3$ | H | H | $C(CH_3)_3$ |
| $CH_2(CH_2)_2CH_3$ | $CH_2(CH_2)_2CH_3$ | H | H | $C(CH_3)_3$ |
| $CH_3$ | $CH_3$ | $CH_3$ | H | $C(CH_3)_3$ |
| $CH_3$ | $CH_3$ | $CH_3$ | $CH_3$ | $C(CH_3)_3$ |
| H | H | H | H | $CH(CH_3)_2$ |
| H | H | H | H | $CH(CH_3)CH_2CH_3$ |
| $CH_3$ | H | H | H | $CH(CH_3)_2$ |
| $CH_3$ | $CH_3$ | H | H | $CH(CH_3)_2$ |
| $CH(CH_3)_2$ | $CH(CH_3)_2$ | H | H | $CH(CH_3)_2$ |
| $CH(CH_3)_2$ | $CH(CH_3)_2$ | H | H | $C(CH_3)_3$ |
| $CH_3$ | $CH_3$ | H | H | H |
| $CH_3$ | H | H | $CH_3$ | H |
| $CH_3$ | H | H | H | $CH_3$ |
| H | H | $CH_3$ | $CH_3$ | H |
| $CH_3$ | $CH_3$ | H | H | $CH_3$ |
| $CH_3$ | $CH_3$ | $CH_3$ | H | $CH_3$ |
| $CH_3$ | $CH_3$ | $CH_3$ | $CH_3$ | $CH_3$ |
| $C_2H_5$ | $C_2H_5$ | H | H | H |
| $C_2H_5$ | $C_2H_5$ | H | H | $C_2H_5$ |
| $C_2H_5$ | $C_2H_5$ | H | H | $C(CH_3)_3$ |
| $CH_2CH_2CH_3$ | $CH_2CH_2CH_3$ | H | H | $CH_2CH_2CH_3$ |
| $CH_2(CH_2)_2CH_3$ | $CH_2(CH_2)_2CH_3$ | H | H | $CH_2(CH_2)_2CH_3$ |
| $CH_2(CH_2)_3CH_3$ | $CH_2(CH_2)_3CH_3$ | H | H | $CH_2(CH_2)_3CH_3$ |
| $CH_2(CH_2)_4CH_3$ | $CH_2(CH_2)_4CH_3$ | H | H | $CH_2(CH_2)_4CH_3$ |
| $CH_2(CH_2)_5CH_3$ | $CH_2(CH_2)_5CH_3$ | H | H | $CH_2(CH_2)_5CH_3$ |
| $CH_2(CH_2)_6CH_3$ | $CH_2(CH_2)_6CH_3$ | H | H | $CH_2(CH_2)_6CH_3$ |
| H | H | H | H | F |
| H | H | H | H | Cl |
| H | H | H | H | Br |
| H | H | H | H | I |
| H | H | $CH_3$ | H | Cl |
| H | H | $CH_3$ | $CH_3$ | Cl |
| $CH_3$ | H | $CH_3$ | $CH_3$ | Cl |
| $CH_3$ | $CH_3$ | $CH_3$ | $CH_3$ | Cl |
| $CH_3$ | $CH_3$ | $CH_3$ | $CH_3$ | Br |
| $CH_3$ | $CH_3$ | $CH_3$ | $CH_3$ | F |
| $CH_3$ | $CH_3$ | Cl | H | H |
| $CH_3$ | $CH_3$ | Cl | Cl | H |

TABLE 1-continued

Illustrative Examples of Substituted Phenylsulfur Trifluoride Compounds of
Formula (I) Showing $R^{1a}$, $R^{1b}$, $R^{2a}$, $R^{2b}$, and $R^3$ Combinations
Based On Substitutions Into Formula (I)

| $R^{1a}$ | $R^{1b}$ | $R^{2a}$ | $R^{2b}$ | $R^3$ |
|---|---|---|---|---|
| $CH_3$ | $CH_3$ | Cl | H | $CH_3$ |
| $CH_3$ | $CH_3$ | Cl | Cl | $CH_3$ |
| $CH_3$ | $CH_3$ | Cl | Cl | $CH_2CH_3$ |
| $CH_3$ | $CH_3$ | Cl | H | $CH(CH_3)_2$ |
| $CH_3$ | $CH_3$ | Cl | Cl | $CH(CH_3)_2$ |
| $CH_3$ | $CH_3$ | Cl | H | $C(CH_3)_3$ |
| $CH_3$ | $CH_3$ | Cl | Cl | $C(CH_3)_3$ |
| $CH_3$ | $CH_3$ | F | H | $C(CH_3)_3$ |
| $CH_3$ | $CH_3$ | F | F | $C(CH_3)_3$ |
| $CH_2OCH_3$ | H | H | H | H |
| $CH(CH_3)OCH_3$ | H | H | H | H |
| $C(CH_3)_2OCH_3$ | H | H | H | H |
| $CH_2CH_2OCH_3$ | H | H | H | H |
| $CH_2OCH_2CH_3$ | H | H | H | H |
| $CH_2OCH_2CH_2CH_3$ | H | H | H | H |
| $CH_2OCH(CH_3)_2$ | H | H | H | H |
| $CH_2OCH_2(CH_2)_2CH_3$ | H | H | H | H |
| $CH_2OC(CH_3)_3$ | H | H | H | H |
| $CH_2OCH_2CH_2OCH_3$ | H | H | H | H |
| $CH_2OCH_2CH_2OCH_2CH_3$ | H | H | H | H |
| $CH_2OCH_2CH_2CH_2OCH_3$ | H | H | H | H |
| $CH_2O(CH_2CH_2O)_2CH_3$ | H | H | H | H |
| $CH_2OCH_3$ | $CH_2OCH_3$ | H | H | H |
| $CH_2OCH_3$ | H | $CH_2OCH_3$ | H | H |
| $CH_2OCH_3$ | H | H | $CH_2OCH_3$ | H |
| $CH_2OCH_3$ | H | H | H | $CH_2OCH_3$ |
| $CH_2OCH_3$ | $CH_2OCH_3$ | $CH_2OCH_3$ | H | H |
| $CH_2OCH_3$ | $CH_2OCH_3$ | H | H | $CH_2OCH_3$ |
| $CH(CH_3)OCH_3$ | $CH(CH_3)OCH_3$ | H | H | $CH(CH_3)OCH_3$ |
| $C(CH_3)_2OCH_3$ | $C(CH_3)_2OCH_3$ | H | H | $C(CH_3)_2OCH_3$ |
| $CH_2OCH_2CH_3$ | $CH_2OCH_2CH_3$ | H | H | H |
| $CH_2OCH_2CH_2CH_3$ | $CH_2OCH_2CH_2CH_3$ | H | H | H |
| $CH_2OCH(CH_3)_2$ | $CH_2OCH(CH_3)_2$ | H | H | H |
| $CH_2OCH_2(CH_2)_2CH_3$ | $CH_2OCH_2(CH_2)_2CH_3$ | H | H | H |
| $CH_2OCH_2CH(CH_3)_2$ | $CH_2OCH_2CH(CH_3)_2$ | H | H | H |
| $CH_2OCH(CH_3)CH_2CH_3$ | $CH_2OCH(CH_3)CH_2CH_3$ | H | H | H |
| $CH_2OC(CH_3)_3$ | $CH_2OC(CH_3)_3$ | H | H | H |
| $CH_2OCH_2C(CH_3)_3$ | $CH_2OCH_2C(CH_3)_3$ | H | H | H |
| $CH_2OCH_3$ | $CH_3$ | H | H | H |
| $CH_2OCH_3$ | H | $CH_3$ | H | H |
| $CH_2OCH_3$ | H | H | $CH_3$ | H |
| $CH_2OCH_3$ | H | H | H | $CH_3$ |
| $CH_2OCH_3$ | $CH_3$ | H | H | $CH_3$ |
| $CH_2OCH_3$ | $CH_3$ | H | H | $CH(CH_3)_2$ |
| $CH_2OCH_3$ | $CH_3$ | H | H | $C(CH_3)_3$ |
| $CH_2OCH_3$ | $CH_2OCH_3$ | H | H | $CH_3$ |
| $CH_2OCH_3$ | $CH_2OCH_3$ | H | H | $CH_2CH_3$ |
| $CH_2OCH_3$ | $CH_2OCH_3$ | H | H | $CH_2CH_2CH_3$ |
| $CH_2OCH_3$ | $CH_2OCH_3$ | H | H | $CH(CH_3)_2$ |
| $CH_2OCH_3$ | $CH_2OCH_3$ | H | H | $C(CH_3)_3$ |
| $CH_2OCH_3$ | $CH_2OCH_3$ | Cl | H | $C(CH_3)_3$ |
| $CH_2OCH_3$ | $CH_2OCH_3$ | Cl | Cl | $C(CH_3)_3$ |
| $CH_2OCH_3$ | $CH_2OCH_3$ | F | H | $C(CH_3)_3$ |
| $CH_2OCH_3$ | $CH_2OCH_3$ | F | F | $C(CH_3)_3$ |
| $CH_2OCH_3$ | $CH_2OCH_3$ | H | H | F |
| $CH_2OCH_3$ | $CH_2OCH_3$ | H | H | Cl |
| $CH_2OCH_2CH_3$ | $CH_2OCH_2CH_3$ | H | H | $C(CH_3)_3$ |
| $CH_2OCH_2CH_2CH_3$ | $CH_2OCH_2CH_2CH_3$ | H | H | $C(CH_3)_3$ |
| $CH_2OCH(CH_3)_2$ | $CH_2OCH(CH_3)_2$ | H | H | $C(CH_3)_3$ |
| $CH_2OCH_2CH_2CH_2CH_3$ | $CH_2OCH_2CH_2CH_2CH_3$ | H | H | $C(CH_3)_3$ |
| $CH_2OCH_2CH(CH_3)_2$ | $CH_2OCH_2CH(CH_3)_2$ | H | H | $C(CH_3)_3$ |
| $CH_2OCH(CH_3)CH_2CH_3$ | $CH_2OCH(CH_3)CH_2CH_3$ | H | H | $C(CH_3)_3$ |
| $CH_2OC(CH_3)_2$ | $CH_2OC(CH_3)_2$ | H | H | $C(CH_3)_3$ |
| $CH(CH_3)OCH_3$ | $CH(CH_3)OCH_3$ | H | H | H |
| $C(CH_3)_2OCH_3$ | $C(CH_3)_2OCH_3$ | H | H | H |
| $C(CH_3)_2OCH_3$ | $C(CH_3)_2OCH_3$ | H | H | $C(CH_3)_3$ |
| $CH_2OCH_2CH_2OCH_3$ | $CH_2OCH_2CH_2OCH_3$ | H | H | $C(CH_3)_3$ |
| $CH_2OCH_2CH_2CH_2OCH_3$ | $CH_2OCH_2CH_2CH_2OCH_3$ | H | H | $C(CH_3)_3$ |
| $CH_2O(CH_2CH_2O)_2CH_3$ | $CH_2O(CH_2CH_2O)_2CH_3$ | H | H | $C(CH_3)_3$ |
| $CH_2CH_2OCH_3$ | $CH_2CH_2OCH_3$ | H | H | $C(CH_3)_3$ |
| $CH_2CH_2OCH_2CH_3$ | $CH_2CH_2OCH_2CH_3$ | H | H | $C(CH_3)_3$ |
| $CH_2CH_2OCH_2CH_2OCH_3$ | $CH_2CH_2OCH_2CH_2OCH_3$ | H | H | $C(CH_3)_3$ |

Embodiments of formula (I) can be compounds represented by formula (Ia):

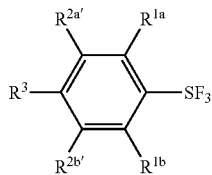

(Ia)

in which $R^{1a}$ and $R^{1b}$ are independently a hydrogen atom; a primary or secondary alkyl group having from one to eight carbon atoms; or a primary, secondary, or tertiary alkyl group having two to eight carbon atoms and at least one ether linkage; and $R^{2a'}$ and $R^{2b'}$ are independently a hydrogen atom or a halogen atom; and $R^3$ is a hydrogen atom; a halogen atom; a primary, secondary, or tertiary alkyl group having from one to eight atoms; or a primary, secondary, or tertiary alkyl group having two to eight carbon atoms and at least one ether linkage;

provided that, when $R^3$ is a hydrogen atom, $R^{1a}$ and $R^{1b}$ are independently a primary or secondary alkyl group having from one to eight carbon atoms or at least one of $R^{1a}$ and $R^{1b}$ is a primary, secondary, or tertiary alkyl group having two to eight carbon atoms and at least one ether linkage, and, when $R^3$ is a primary alkyl group having one to eight carbon atoms, at least one of $R^{1a}$ and $R^{1b}$ is a primary or secondary alkyl group having from one to eight carbon atoms, or a primary, secondary, or tertiary alkyl group having two to eight carbon atoms and at least one ether linkage.

Examples of the alkyl groups of $R^{1a}$, $R^{1b}$ and $R^3$ are the same as above. Examples of preferred halogen atoms of $R^3$ are as previously described, and examples of preferred halogen atoms of $R^{2a'}$ and $R^{2b'}$ are the same as the halogen atoms of $R^3$.

In preferred embodiments the alkyl groups of formula (Ia) have from one to four carbon atoms, and the alkyl groups having at least one ether linkage have from two to five carbon atoms. Preferred alkyl groups of $R^3$ are tertiary alkyl groups and the most preferred alkyl group of $R^3$ is tert-butyl group.

Table 1a provides illustrative combinations of $R^{1a}$, $R^{1b}$, $R^{2a'}$, $R^{2b'}$ and $R^3$ for inclusion in formula (Ia).

TABLE 1a

Illustrative Examples of Substituted Phenylsulfur Trifluoride Compounds of Formula (Ia) Showing $R^{1a}$, $R^{1b}$, $R^{2a'}$, $R^{2b'}$, and $R^3$ Combinations Based On Substitutions Into Formula (Ia)

| $R^{1a}$ | $R^{1b}$ | $R^{2a'}$ | $R^{2b'}$ | $R^3$ |
|---|---|---|---|---|
| H | H | H | H | $C(CH_3)_3$ |
| H | H | H | H | $C(CH_3)_2C_2H_5$ |
| H | H | H | H | $C(CH_3)_2(CH_2)_2CH_3$ |
| H | H | H | H | $C(CH_3)_2(CH_2)_3CH_3$ |
| H | H | H | H | $C(CH_3)_2(CH_2)_4CH_3$ |
| $CH_3$ | H | H | H | $C(CH_3)_3$ |
| $CH_3$ | $CH_3$ | H | H | $C(CH_3)_3$ |
| $CH_3$ | $CH_3$ | Cl | H | $C(CH_3)_3$ |
| $CH_3$ | $CH_3$ | Cl | Cl | $C(CH_3)_3$ |
| $CH_3$ | $CH_3$ | F | H | $C(CH_3)_3$ |
| $CH_3$ | $CH_3$ | F | F | $C(CH_3)_3$ |
| H | H | H | H | $CH(CH_3)_2$ |
| H | H | H | H | $CH(CH_3)C_2H_5$ |
| $CH_3$ | H | H | H | $CH(CH_3)_2$ |
| $CH_3$ | $CH_3$ | H | H | $CH(CH_3)_2$ |
| $CH(CH_3)_2$ | $CH(CH_3)_2$ | H | H | $CH(CH_3)_2$ |
| $CH(CH_3)_2$ | $CH(CH_3)_2$ | H | H | $C(CH_3)_3$ |
| $CH_3$ | $CH_3$ | H | H | H |
| $CH_3$ | H | H | H | $CH_3$ |
| $CH_3$ | $CH_3$ | H | H | $CH_3$ |
| $CH_3$ | $CH_3$ | Cl | H | $CH_3$ |
| $CH_3$ | $CH_3$ | Cl | Cl | $CH_3$ |
| $C_2H_5$ | $C_2H_5$ | H | H | H |
| $C_2H_5$ | $C_2H_5$ | H | H | $C_2H_5$ |
| $C_2H_5$ | $C_2H_5$ | H | H | $C(CH_3)_3$ |
| $CH_2CH_2CH_3$ | $CH_2CH_2CH_3$ | H | H | $CH_2CH_2CH_3$ |
| $CH_2(CH_2)_2CH_3$ | $CH_2(CH_2)_2CH_3$ | H | H | $CH_2(CH_2)_2CH_3$ |
| $CH_2(CH_2)_3CH_3$ | $CH_2(CH_2)_3CH_3$ | H | H | $CH_2(CH_2)_3CH_3$ |
| $CH_2(CH_2)_4CH_3$ | $CH_2(CH_2)_4CH_3$ | H | H | $CH_2(CH_2)_4CH_3$ |
| $CH_2(CH_2)_5CH_3$ | $CH_2(CH_2)_5CH_3$ | H | H | $CH_2(CH_2)_5CH_3$ |
| $CH_2(CH_2)_6CH_3$ | $CH_2(CH_2)_6CH_3$ | H | H | $CH_2(CH_2)_6CH_3$ |
| H | H | H | H | F |
| H | H | H | H | Cl |
| H | H | H | H | Br |
| H | H | H | H | I |
| $CH_3$ | H | H | H | Cl |
| $CH_3$ | $CH_3$ | H | H | Cl |
| $CH_3$ | $CH_3$ | H | H | Br |
| $CH_3$ | $CH_3$ | H | H | F |

TABLE 1a-continued

Illustrative Examples of Substituted Phenylsulfur Trifluoride Compounds of
Formula (Ia) Showing $R^{1a}$, $R^{1b}$, $R^{2a'}$, $R^{2b'}$, and $R^3$ Combinations
Based On Substitutions Into Formula (Ia)

| $R^{1a}$ | $R^{1b}$ | $R^{2a'}$ | $R^{2b'}$ | $R^3$ |
|---|---|---|---|---|
| $CH_2OCH_3$ | H | H | H | H |
| $CH_2OCH_2CH_2OCH_3$ | H | H | H | H |
| $CH_2OCH_2CH_2CH_2OCH_3$ | H | H | H | H |
| $CH_2OCH_2CH_2OCH_2CH_3$ | H | H | H | H |
| $CH_2O(CH_2CH_2O)_2CH_3$ | H | H | H | H |
| H | H | H | H | $CH_2OCH_3$ |
| $CH_2OCH_3$ | $CH_2OCH_3$ | H | H | H |
| $CH_2OCH_3$ | H | H | H | $CH_2OCH_3$ |
| $CH_2OCH_3$ | $CH_2OCH_3$ | H | H | $CH_2OCH_3$ |
| $CH(CH_3)OCH_3$ | $CH(CH_3)OCH_3$ | H | H | H |
| $CH(CH_3)OCH_3$ | $CH(CH_3)OCH_3$ | H | H | $CH(CH_3)OCH_3$ |
| $C(CH_3)_2OCH_3$ | $C(CH_3)_2OCH_3$ | H | H | H |
| $C(CH_3)_2OCH_3$ | $C(CH_3)_2OCH_3$ | H | H | $C(CH_3)_2OCH_3$ |
| $CH_2OCH_2CH_2OCH_3$ | $CH_2OCH_2CH_2OCH_3$ | H | H | H |
| $CH_2OCH_3$ | $CH_2OCH_3$ | H | H | $CH_3$ |
| $CH_2OCH_3$ | $CH_2OCH_3$ | H | H | $C(CH_3)_3$ |
| $CH_2OCH_3$ | $CH_2OCH_3$ | Cl | H | $C(CH_3)_3$ |
| $CH_2OCH_3$ | $CH_2OCH_3$ | Cl | Cl | $C(CH_3)_3$ |
| $CH_2OCH_3$ | $CH_2OCH_3$ | F | H | $C(CH_3)_3$ |
| $CH_2OCH_3$ | $CH_2OCH_3$ | F | F | $C(CH_3)_3$ |
| $CH_2OCH_2CH_3$ | $CH_2OCH_2CH_3$ | H | H | $C(CH_3)_3$ |
| $CH_2OCH_2CH_2CH_3$ | $CH_2OCH_2CH_2CH_3$ | H | H | $C(CH_3)_3$ |
| $CH_2OCH(CH_3)_2$ | $CH_2OCH(CH_3)_2$ | H | H | $C(CH_3)_3$ |
| $CH_2OCH_2CH_2CH_2CH_3$ | $CH_2OCH_2CH_2CH_2CH_3$ | H | H | $C(CH_3)_3$ |
| $CH_2OCH_2CH_2(CH_3)_2$ | $CH_2OCH_2CH_2(CH_3)_2$ | H | H | $C(CH_3)_3$ |
| $CH_2OCH(CH_3)CH_2CH_3$ | $CH_2OCH(CH_3)CH_2CH_3$ | H | H | $C(CH_3)_3$ |
| $CH_2OC(CH_3)_3$ | $CH_2OC(CH_3)_3$ | H | H | $C(CH_3)_3$ |
| $CH(CH_3)OCH_3$ | $CH(CH_3)OCH_3$ | H | H | $C(CH_3)_3$ |
| $C(CH_3)_2OCH_3$ | $C(CH_3)_2OCH_3$ | H | H | $C(CH_3)_3$ |
| $CH_2CH_2OCH_3$ | $CH_2CH_2OCH_3$ | H | H | $C(CH_3)_3$ |
| $CH_2OCH_2CH_2OCH_3$ | $CH_2OCH_2CH_2OCH_3$ | H | H | $C(CH_3)_3$ |
| $CH_2OCH_3$ | $CH_2OCH_3$ | H | H | Cl |
| $CH_2OCH_3$ | $CH_2OCH_3$ | H | H | F |
| $CH_2OCH_2CH_2OCH_3$ | H | H | H | H |
| $CH_2OCH_3$ | $CH_3$ | H | H | $CH_3$ |
| $CH_2OCH_3$ | $CH_3$ | H | H | $C(CH_3)_3$ |

Preferred embodiments of formula (Ia) are compounds having a formula (II):

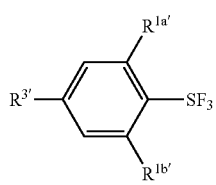

(II)

in which $R^{1a'}$ and $R^{1b'}$ are independently a hydrogen atom or a primary or secondary alkyl group having from one to eight carbon atoms; and $R^{3'}$ is a hydrogen atom, a halogen atom, or a primary, secondary, or tertiary alkyl group having from one to eight carbon atoms, provided that, when $R^{3'}$ is a hydrogen atom, $R^{1a'}$ and $R^{1b'}$ are independently primary or secondary alkyl groups having from one to eight carbon atoms and, when $R^{3'}$ is a primary alkyl group having from one to eight carbon atoms, at least one of $R^{1a'}$ and $R^{1b'}$ is a primary or secondary alkyl group having from one to eight carbon atoms. Examples of the primary or secondary alkyl groups of $R^{1a'}$ and $R^{1b'}$ having one to eight carbon atoms are the same as examples of the primary or secondary alkyl groups of $R^{1a}$ and $R^{1b}$ having one to eight carbon atoms, which are described previously. Examples of the primary, secondary, or tertiary alkyl groups of $R^{3'}$ having from one to eight carbon atoms are the same as examples of the primary, secondary, or tertiary alkyl groups of $R^3$ having from one to eight carbon atoms, which are described previously. Examples of the halogen atoms of $R^{3'}$ are the same as examples of the halogen atoms of $R^3$, which are described previously. In preferred embodiments the alkyl groups of formula (II) have from one to four carbon atoms. More preferred alkyl groups of $R^{3'}$ are tertiary alkyl groups and the most preferred alkyl group of $R^{3'}$ is tert-butyl group.

Table 2 provides illustrative combinations of $R^{1a'}$, $R^{1b'}$ and $R^{3'}$ for inclusion in formula (II).

TABLE 2

Illustrative Examples of Substituted Phenylsulfur Trifluoride Compounds
of Formula (II) Showing $R^{1a'}$, $R^{1b'}$, and $R^{3'}$ Combinations
Based On Substitutions Into Formula (II)

| $R^{1a'}$ | $R^{1b'}$ | $R^{3'}$ |
|---|---|---|
| H | H | $C(CH_3)_3$ |
| H | H | $C(CH_3)_2C_2H_5$ |
| H | H | $C(CH_3)_2(CH_2)_2CH_3$ |
| H | H | $C(CH_3)_2(CH_2)_3CH_3$ |
| H | H | $C(CH_3)_2(CH_2)_4CH_3$ |
| $CH_3$ | H | $C(CH_3)_3$ |
| $CH_3$ | $CH_3$ | $C(CH_3)_3$ |

TABLE 2-continued

Illustrative Examples of Substituted Phenylsulfur Trifluoride Compounds of Formula (II) Showing $R^{1a'}$, $R^{1b'}$, and $R^{3'}$ Combinations Based On Substitutions Into Formula (II)

| $R^{1a'}$ | $R^{1b'}$ | $R^{3'}$ |
|---|---|---|
| H | H | $CH(CH_3)_2$ |
| H | H | $CH(CH_3)C_2H_5$ |
| $CH_3$ | H | $CH(CH_3)_2$ |
| $CH_3$ | $CH_3$ | $CH(CH_3)_2$ |
| $CH(CH_3)_2$ | $CH(CH_3)_2$ | $CH(CH_3)_2$ |
| $CH(CH_3)_2$ | $CH(CH_3)_2$ | $C(CH_3)_3$ |
| $CH_3$ | $CH_3$ | H |
| $CH_3$ | H | $CH_3$ |
| $CH_3$ | $CH_3$ | $CH_3$ |
| $C_2H_5$ | $C_2H_5$ | H |
| $C_2H_5$ | $C_2H_5$ | $C_2H_5$ |
| $C_2H_5$ | $C_2H_5$ | $C(CH_3)_3$ |
| $CH_2CH_2CH_3$ | $CH_2CH_2CH_3$ | $CH_2CH_2CH_3$ |
| $CH_2(CH_2)_2CH_3$ | $CH_2(CH_2)_2CH_3$ | $CH_2(CH_2)_2CH_3$ |
| $CH_2(CH_2)_3CH_3$ | $CH_2(CH_2)_3CH_3$ | $CH_2(CH_2)_3CH_3$ |
| $CH_2(CH_2)_4CH_3$ | $CH_2(CH_2)_4CH_3$ | $CH_2(CH_2)_4CH_3$ |
| $CH_2(CH_2)_5CH_3$ | $CH_2(CH_2)_5CH_3$ | $CH_2(CH_2)_5CH_3$ |
| $CH_2(CH_2)_6CH_3$ | $CH_2(CH_2)_6CH_3$ | $CH_2(CH_2)_6CH_3$ |
| H | H | F |
| H | H | Cl |
| H | H | Br |
| H | H | I |
| $CH_3$ | H | Cl |
| $CH_3$ | $CH_3$ | Cl |
| $CH_3$ | $CH_3$ | Br |
| $CH_3$ | $CH_3$ | F |

Another preferred embodiment of formula (Ia) is compounds having a formula (Ib):

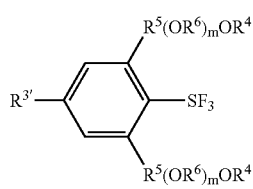

(Ib)

in which $R^{3'}$ is a hydrogen atom, a halogen atom, or a primary, secondary, or tertiary alkyl group having from one to eight carbon atoms;

$R^4$ is a primary, secondary, or tertiary alkyl group; and $R^5$ and $R^6$ are independently an alkylene group; the total carbon number of $R^4$, $R^5$ and $R^6$ is eight or less, and m is 0 or 1.

In preferred embodiments the alkyl groups of formula (Ib) have four carbons or less; the alkylene groups of formula (Ib) have four carbons or less; and m is 0. Preferred $R^{3'}$ is a hydrogen atom or a tertiary alkyl group, more preferred $R^{3'}$ is a tertiary alkyl group, and most preferred $R^{3'}$ is tert-butyl group.

Examples of alkyl groups of $R^{3'}$ having a primary, secondary, or tertiary alkyl group having from one to eight atoms are the same as described above. Examples of the halogen atoms of $R^3$ are the same as described above.

The primary, secondary, or tertiary alkyl groups of $R^4$ include; primary alkyl groups such as $CH_3$, $CH_2CH_3$, $CH_2(CH_2)_nCH_3$ (n=1-5), $CH_2CH(CH_3)_2$, and $CH_2C(CH_3)_3$, secondary alkyl groups such as $CH(CH_3)_2$, $CH(CH_3)CH_2CH_3$, and $CH(CH_3)CH_2(CH_2)_nCH_3$ (n=1-3), and tertiary alkyl groups such as $C(CH_3)_3$, $C(CH_3)_2CH_2CH_3$, and $C(CH_3)_2$ $CH_2(CH_2)_nCH_3$ (n=1, 2). From the viewpoint of stability for a compound having formula (Ib), $R^4$ is preferably a primary or secondary alkyl group. Preferred primary alkyl groups of $R^4$ include: $CH_3$, $CH_2CH_3$, $CH_2(CH_2)_nCH_3$ (n=1, 2), $CH_2CH(CH_3)_2$, and $CH_2C(CH_3)_3$ and preferred secondary alkyl groups of $R^4$ include: $CH(CH_3)_2$ and $CH(CH_3)$ $CH_2CH_3$. One preferred primary alkyl group of $R^4$ is $CH_3$ and most preferred secondary alkyl group of $R^4$ includes $CH(CH_3)_2$.

The alkylene groups of $R^5$ and $R^6$ include; $CH_2$, $CH_2CH_2$, $CH_2(CH_2)_nCH_2$ (n=1, 2), $CH(CH_3)$, $CH(CH_2CH_3)$, $CH_2CH$ $(CH_3)$, $CH(CH_3)CH_2$, $C(CH_3)_2$, $CH_2C(CH_3)_2$, $C(CH_3)_2CH_2$ and $CH[CH(CH_3)_2]$. Preferred alkylene groups of $R^5$ are $CH_2$, $CH_2CH_2$, and $CH_2CH_2CH_2$, and most preferred alkylene groups of $R^5$ are $CH_2$. Preferred alkylene groups of $R^6$ are $CH_2CH_2$, $CH_2CH(CH_3)$, $CH(CH_3)CH_2$ and $CH_2CH_2CH_2$, and most preferred alkylene group of $R^6$ is $CH_2CH_2$.

Table 2a provides illustrative combinations of $R^{3'}$, $R^4$, $R^5$, $R^6$, and m for inclusion in formula (Ib).

TABLE 2a

Illustrative Examples of Substituted Phenylsulfur Trifluoride Compounds of Formula (Ib) Showing $R^{3'}$, $R^4$, $R^5$, $R^6$ and m Combinations Based On Substitutions Into Formula (Ib)

| $R^{3'}$ | $R^5(OR^6)_mO$ (m = 0 or 1) | $R^4$ |
|---|---|---|
| H | $CH_2O$ | $CH_3$ |
| H | $CH_2O$ | $C_2H_5$ |
| H | $CH_2O$ | $CH_2CH_2CH_3$ |
| H | $CH_2O$ | $CH(CH_3)_2$ |
| H | $CH_2O$ | $CH_2(CH_2)_2CH_3$ |
| H | $CH_2O$ | $CH(CH_3)CH_2CH_3$ |
| H | $CH_2O$ | $CH_2CH(CH_3)_2$ |
| H | $CH_2O$ | $C(CH_3)_3$ |
| H | $CH_2O$ | $CH_2C(CH_3)_3$ |
| H | $CH(CH_3)O$ | $CH_3$ |
| H | $C(CH_3)_2O$ | $CH_3$ |
| H | $CH(CH_2CH_3)O$ | $CH_3$ |
| H | $CH[CH(CH_3)_2]O$ | $CH_3$ |
| H | $CH_2CH_2O$ | $CH_3$ |
| H | $CH_2CH(CH_3)O$ | $CH_3$ |
| H | $CH(CH_3)CH_2O$ | $CH_3$ |
| H | $CH_2C(CH_3)_2O$ | $CH_3$ |
| H | $C(CH_3)_2CH_2O$ | $CH_3$ |
| H | $CH_2OCH_2CH_2O$ | $CH_3$ |
| $CH_3$ | $CH_2O$ | $CH_3$ |
| $C_2H_5$ | $CH_2O$ | $CH_3$ |
| $CH_2CH_2CH_3$ | $CH_2O$ | $CH_3$ |
| $CH(CH_3)_2$ | $CH_2O$ | $CH_3$ |
| $CH_2(CH_2)_2CH_3$ | $CH_2O$ | $CH_3$ |
| $CH(CH_3)CH_2CH_3$ | $CH_2O$ | $CH_3$ |
| $CH_2CH(CH_3)CH_3$ | $CH_2O$ | $CH_3$ |
| $C(CH_3)_3$ | $CH_2O$ | $CH_3$ |
| $C(CH_3)_3$ | $CH_2O$ | $C_2H_5$ |
| $C(CH_3)_3$ | $CH_2O$ | $CH_2CH_2CH_3$ |
| $C(CH_3)_3$ | $CH_2O$ | $CH(CH_3)_2$ |
| $C(CH_3)_3$ | $CH_2O$ | $CH_2CH_2CH_2CH_3$ |
| $C(CH_3)_3$ | $CH_2O$ | $CH_2CH(CH_3)_2$ |
| $C(CH_3)_3$ | $CH_2O$ | $CH(CH_3)CH_2CH_3$ |
| $C(CH_3)_3$ | $CH_2O$ | $C(CH_3)_3$ |
| $C(CH_3)_3$ | $CH(CH_3)O$ | $CH_3$ |
| $C(CH_3)_3$ | $CH[CH(CH_3)_2]O$ | $CH_3$ |
| $C(CH_3)_3$ | $C(CH_3)_2O$ | $CH_3$ |
| $C(CH_3)_3$ | $CH_2CH_2O$ | $CH_3$ |
| $C(CH_3)_3$ | $CH_2OCH_2CH_2O$ | $CH_3$ |
| $C(CH_3)_3$ | $CH_2CH_2OCH_2CH_2O$ | $CH_3$ |
| F | $CH_2O$ | $CH_3$ |
| Cl | $CH_2O$ | $CH_3$ |
| Br | $CH_2O$ | $CH_3$ |
| I | $CH_2O$ | $CH_3$ |

The fluorinating agents of the present invention are typically provided in substantially pure form, for example at least 50% pure, more typically 60% pure, advantageously at least 75% pure and preferably at least 85% or 90% pure. All percentages are calculated on a weight/weight basis.

The fluorinating agents of the present invention may also be combination of any two or more fluorinating agents described herein (see Examples in Table 5).

It will be understood by one of skill in the relevant art that certain compounds of the invention may comprise one or more chiral centers so that the compounds may exist as stereoisomers, including diastereoisomers and enantiomers. It is envisioned that all such compounds be within the scope of the present invention, including all such stereoisomers, and mixtures thereof, including racemates.

Fluorinating agents of the invention may be prepared according to the methods as described in the Examples below, see particularly Examples 2, 3, 3a-c, 4-15, and 15a-g. In addition, methods reported in the literature may be modified to produce various agents illustrated in Tables 1, 1a, 2 and 2a [see J. Am. Chem. Soc., Vol. 84, pp 3058-3063 (1962); Synthetic Communications, Vol. 33, No. 14, pp 2505-2509 (2003)].

Typically, the starting materials for synthesis of the substituted phenylsulfur trifluorides of the invention are the corresponding substituted biphenyl disulfides, which are either commercially available, prepared by oxidation of the corresponding substituted thiophenols, prepared from the corresponding substituted benzenesulfonyl halides (see for example the methods as shown in Examples 1, 1a, 1c, and 1d), or are prepared from the corresponding substituted phenyl halides (see for example the methods as shown in Examples 1b, 1e, 1f, 1g, 1h, and 1j).

The present invention provides bis(2,6-dimethyl-3-chloro-4-tert-butylphenyl)disulfide and bis(2,6-dimethyl-3,5-dichloro-4-tert-butylphenyl)disulfide which are useful intermediates for synthesis of the novel substituted phenylsulfur trifluorides of the present invention.

The present invention also provides the compound of formula (Ic);

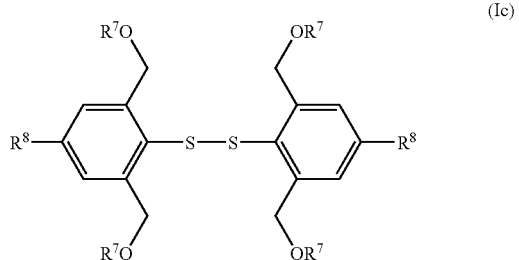

in which:

$R^7$ is a primary, secondary, or tertiary alkyl group having from one to four carbon atoms, and $R^8$ is a hydrogen atom or a primary, secondary, or tertiary alkyl group having from one to four carbon atoms.

The compounds of formula (Ic) are useful intermediates in the synthesis of the novel substituted phenylsulfur trifluorides of the present invention.

Some embodiments of the invention are those compounds of formula (Ic) where primary, secondary, or tertiary alkyl groups of $R^7$ having from one to four carbon atoms include: primary alkyl groups such as $CH_3$, $CH_2CH_3$, $CH_2(CH_2)_n$ $CH_3$ (n=1, 2), and $CH_2CH(CH_3)_2$, secondary alkyl groups such as $CH(CH_3)_2$ and $CH(CH_3)CH_2CH_3$, and tertiary alkyl groups such as $C(CH_3)_3$. More preferred alkyl groups of $R^7$ include: $CH_3$, $CH_2CH_3$, $CH(CH_3)_2$, $CH(CH_3)CH_2CH_3$, $CH_2CH(CH_3)_2$, and $C(CH_3)_3$ and the most preferred alkyl groups of $R^7$ include $CH_3$, $CH_2CH_3$, $CH(CH_3)_2$, $CH_2CH(CH_3)_2$, and $C(CH_3)_3$.

Other embodiments of the invention are those compounds of formula (Ic) where primary, secondary, or tertiary alkyl groups having from one to four carbon atoms of $R^8$ include: $CH_3$, $CH_2CH_3$, $CH_2(CH_2)_nCH_3$ (n=1, 2), $CH(CH_3)_2$, $CH(CH_3)CH_2CH_3$, $CH_2CH(CH_3)_2$, and $C(CH_3)_3$. More preferred alkyl groups having from one to four carbon atoms of $R^8$ include: $CH_3$, $CH_2CH_3$, $CH(CH_3)_2$, $C(CH_3)_3$, and highly preferred alkyl group of $R^8$ includes $C(CH_3)_3$.

While not being tied to any particular mechanism, the unexpected functional activities of the novel substituted phenylsulfur trifluorides of the present invention are due, at least in part, to their relatively high stability. The high stability of these substituted phenylsulfur trifluorides is due at least in part, to high decomposition temperatures and low exothermal heat ($-\Delta H$) (see Examples 16, 16a,b, 17-25, and 25a,b) as compared to more conventional fluorinating agents. These values can be compared to the values for other conventional fluorinating agents (see Table 4), where DAST and Deoxo-Fluor® have a decomposition temperature of about 140° C. and exothermic heat values of 1100-1700 J/g as compared to compounds of the invention where decomposition temperatures of about 175-320° C. and exothermic heat of 350-700 J/g are typical (see Table 4).

The novel phenylsulfur trifluorides of the present invention also have high stability in water as compared to conventional fluorinating agents, such as DAST, and Deoxo-Fluor®, (which are known to be dangerous because of vigorous reaction when contacted with water (see Table 6)). Note that phenylsulfur trifluoride ($PhSF_3$) and p-methylphenylsulfur trifluoride (p-$CH_3C_6H_4SF_3$) are similar to DAST and Deoxy-Fluor. Unexpectedly and surprisingly, the substituted phenylsulfur trifluorides of the invention, such as 2,6-dimethyl-4-tert-butylphenylsulfur trifluoride, 2,6-dimethyl-3,5-dichloro-4-tert-butylphenylsulfur trifluoride, 2,6-bis(methoxymethyl)phenylsulfur trifluoride, 2,6-bis(methoxymethyl)-4-tert-butylphenylsulfur trifluoride, 2,6-bis(ethoxymethyl)-4-tert-butylphenylsulfur trifluoride, 2,6-bis(isopropoxymethyl)-4-tert-butylphenylsulfur trifluoride, 2,6-bis(isobutoxymethyl)-4-tert-butylphenylsulfur trifluoride, and a mixture of 2,6-dimethyl-4-tert-butylphenylsulfur trifluoride and 2,6-dimethyl-3-chloro-4-tert-butylphenylsulfur trifluoride, have little or no reaction when contacted with water. Alkyl groups such as tert-butyl group and alkyl groups having at least one ether linkage brought about unexpected and surprising high stability against water and moisture. Therefore, the phenylsulfur trifluorides of the present invention have high stability, storage stability, safety, safe handling, and safe disposability as compared to many conventional agents.

EXAMPLES

The following examples are provided for illustrative purposes only and are not intended to limit the scope of the invention. Table 3 provides structure names and formulas for reference when reviewing the following examples:

TABLE 3

Substituted Phenylsulfur Trifluorides (Formulas IV, IVa,b, V-XIX) and Starting Materials (Formulas III, IIIa-h):

| Formula Number | Name | Structure |
|---|---|---|
| III | Bis(2,6-dimethyl-4-tert-butylphenyl) disulfide | 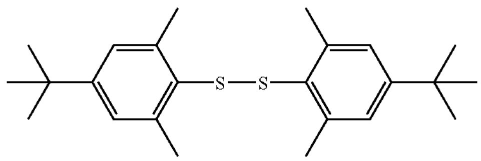 |
| IIIa | Bis(2,6-dimethyl-3-chloro-4-tert-butylphenyl) disulfide | 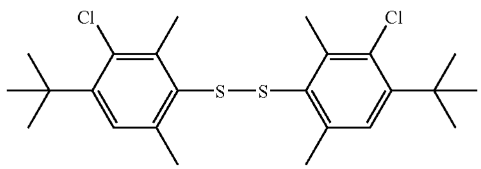 |
| IIIb | Bis(2,6-dimethyl-3,5-dichloro-4-tert-butylphenyl) disulfide | 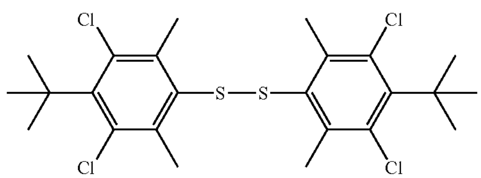 |
| IIIc | Bis[2,6-bis(methoxymethyl)phenyl] disulfide | 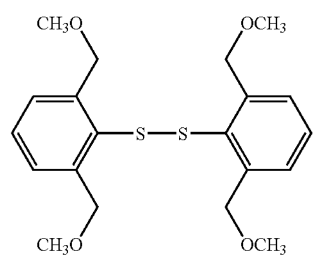 |
| IIId | Bis[2,6-bis(methoxymethyl)-4-tert-butylphenyl] disulfide | 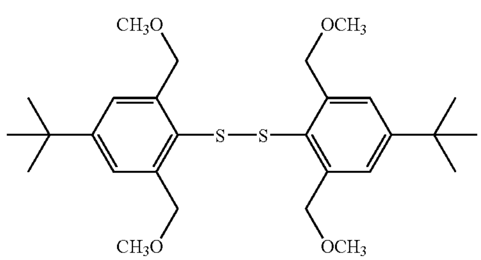 |
| IIIe | Bis[2,6-bis(ethoxymethyl)-4-tert-butylphenyl] disulfide | 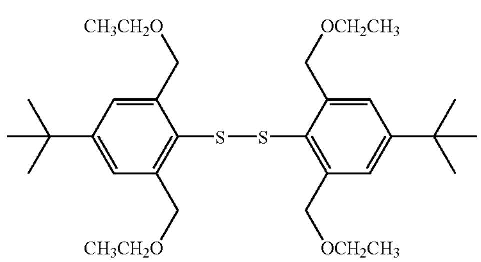 |

TABLE 3-continued

Substituted Phenylsulfur Trifluorides (Formulas IV, IVa,b, V-XIX) and Starting Materials (Formulas III, IIIa-h):

| Formula Number | Name | Structure |
|---|---|---|
| IIIf | Bis[2,6-bis(isopropoxymethyl)-4-tert-butylphenyl] disulfide | 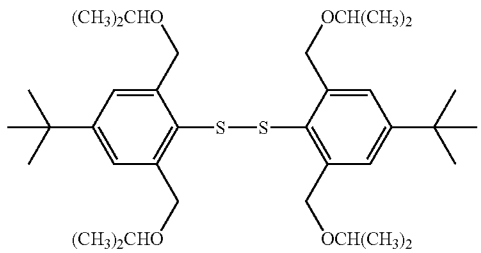 |
| IIIg | Bis[2,6-bis(isobutoxymethyl)-4-tert-butylphenyl] disulfide | 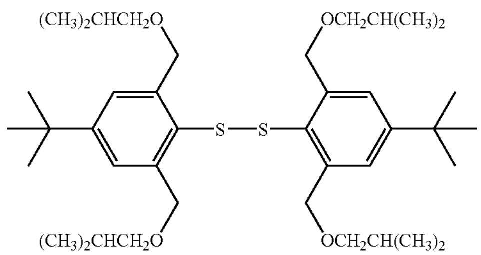 |
| IIIh | Bis[2,6-bis(tert-butoxymethyl)-4-tert-butylphenyl] disulfide | 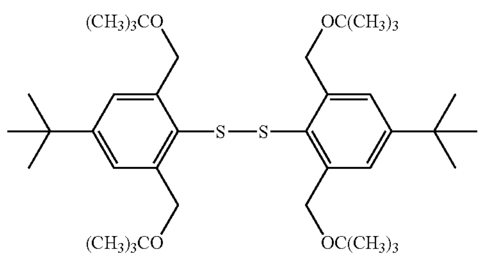 |
| IV | 2,6-Dimethyl-4-tert-butylphenylsulfur trifluoride | 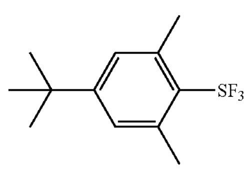 |
| IVa | 2,6-Dimethyl-3-chloro-4-tert-butylphenylsulfur trifluoride | 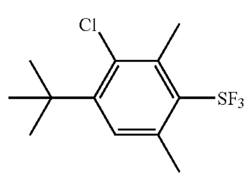 |
| IVb | 2,6-Dimethyl-3,5-dichloro-4-tert-butylphenylsulfur trifluoride | 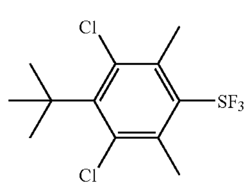 |
| V | 4-tert-Butylphenylsulfur trifluoride | 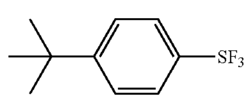 |

TABLE 3-continued

Substituted Phenylsulfur Trifluorides (Formulas IV, IVa,b, V-XIX) and Starting Materials (Formulas III, IIIa-h):

| Formula Number | Name | Structure |
|---|---|---|
| VI | 2,4,6-Trimethylphenylsulfur trifluoride | 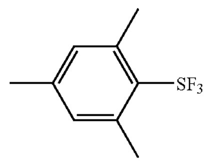 |
| VII | 2,4-Dimethylphenylsulfur trifluoride | 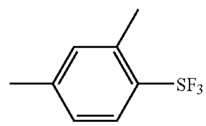 |
| VIII | 2,5-Dimethylphenylsulfur trifluoride | 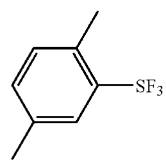 |
| IX | 2,6-Dimethylphenylsulfur trifluoride | 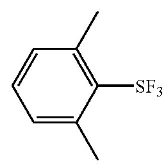 |
| X | 4-Fluorophenylsulfur trifluoride | 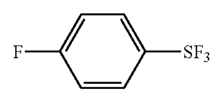 |
| XI | 4-Chlorophenylsulfur trifluoride | 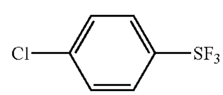 |
| XII | 3-Methyl-4-chlorophenylsulfur trifluoride | 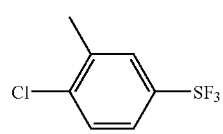 |
| XIII | 2,4,6-Tri(isopropyl)phenylsulfur trifluoride | 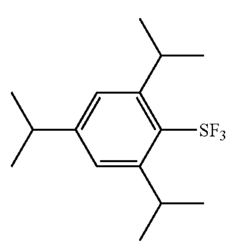 |
| XIV | 2,6-Bis(methoxymethyl)phenyl sulfur trifluoride | 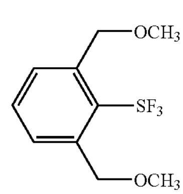 |

TABLE 3-continued

Substituted Phenylsulfur Trifluorides (Formulas IV, IVa,b, V-XIX) and Starting Materials (Formulas III, IIIa-h):

| Formula Number | Name | Structure |
|---|---|---|
| XV | 2,6-Bis(methoxymethyl)-4-tert-butylphenylsulfur trifluoride | 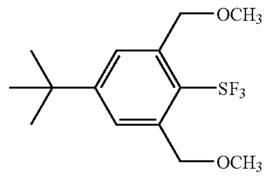 |
| XVI | 2,6-Bis(ethoxymethyl)-4-tert-butylphenylsulfur trifluoride | 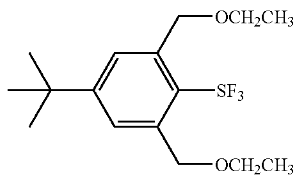 |
| XVII | 2,6-Bis(isopropoxymethyl)-4-tert-butylphenylsulfur trifluoride | 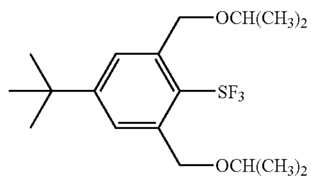 |
| XVIII | 2,6-Bis(isobutoxymethyl)-4-tert-butylphenylsulfur trifluoride | 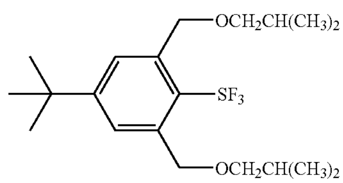 |
| XIX | 2,6-Bis(tert-butoxymethyl)-4-tert-butylphenylsulfur trifluoride | 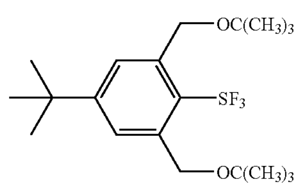 |

Example 1

Preparation of bis(2,6-dimethyl-4-tert-butylphenyl)disulfide

The following reaction scheme is provided as illustrative:

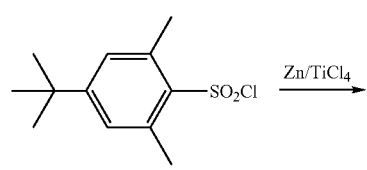

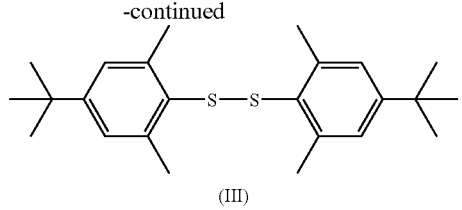

(III)

A two liter, three-neck flask, was obtained. A condenser with a drying tube, a thermometer, and a dropping funnel were each attached to the flask. Zinc dust (<10 micron, 43.6 g, 0.667 mol) and anhydrous tetrahydrofuran (400 mL) were added to the flask. The mixture was stirred and cooled on an ice-water bath and 58.6 ml (0.534 mmol) of titanium tetrachloride added drop wise (~45 min). During the entire addition of titanium tetrachloride, the temperature of the mixture was maintained below 25° C. Once the addition was complete, a solution of 2,6-dimethyl-4-tert-butylbenzenesulfonyl chloride (69.48 g, 0.267 mol) in 200 mL of anhydrous tetrahydrofuran was added drop wise (~60 min). During the entire addition of the material, the temperature of the mixture was maintained below 20° C. At the conclusion of the 2,6-dimethyl-4-tert-butylbenzenesulfonyl chloride addition, the ice-water bath was removed, the mixture was allowed to stir an additional 30 min. The mixture was then heated on an oil bath at 60° C. for 4 hours. The mixture was then cooled to room temperature and 800 mL of 1N hydrochloric acid and 300 mL of ice water added. The resultant pale yellow precipitates were collected by filtration and washed with water (300 mL×3). The precipitate was then dried under vacuum and the precipitates recrystallized from hexanes, giving 33.1 g bis(2,6-dimethyl-4-tert-butylphenyl)disulfide (see Formula III, Table 3). The yield of the reaction was 70% and the material had the following spectral data: $^1$H NMR (CDCl$_3$) δ 7.04 (s, 4H, aromatic protons (Ar—H)), 2.23 (s, 12H, CH$_3$), 1.30 (s, 18H, C(CH$_3$)$_3$).

The present example illustrates the utility of the present invention for synthesizing intermediates for producing fluorinating agents that can be used to produce fluorine-containing compounds.

Example 1a

Alternative Preparation of bis(2,6-dimethyl-4-tert-butylphenyl)disulfide

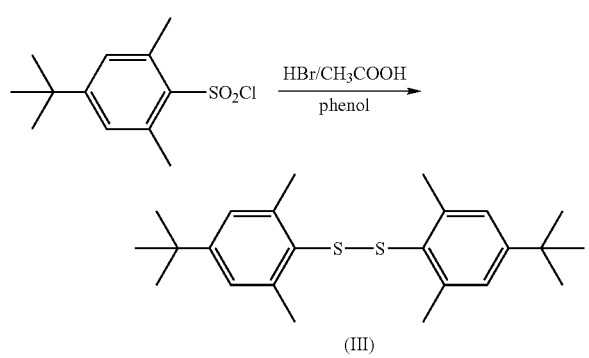

A 5 liter, 3 neck, jacketed round bottom flask was set-up with mechanical stirrer, internal thermometer, and reflux condenser with a gas exit through a plastic tube into an acid trap. The flask was charged with 885.8 g (3.40 mol) of 2,6-dimethyl-4-tert-butylbenzenesulfonyl chloride, 388 g (4.12 mol) of phenol, and 1000 mL of glacial acetic acid. The reaction was heated to 35-40° C. with stirring until all reactants were dissolved. In the solution, 1600 mL of 33 wt % hydrogen bromide/acetic acid solution was added, essentially all at once, but slowly and carefully. The reaction appeared to begin at once with darkening of the solution and a significant initial release of acid gas. With the jacket held at 35° C., a strong but steady exotherm raised the internal temperature to a maximum of 47° C. over 20 min. When the temperature began to subside, heating was applied and the jacket was raised to 60° C., and held for approximately 6 hours total. The reaction was then set-up for simple vacuum distillation to remove as much acid solvents as possible. A total of 2350 mL was removed, leaving a thick, dark slurry in the flask. Water (1000-1500 mL) was added to the reaction mass, followed by sodium hydroxide to make the solution alkaline with a pH of approximately 10 to remove acetic acid and other products, brominated phenols such as bromophenols and 2,4-dibromophenol. The dark biphase slurry was then extracted with 2:1 ether/pentane. The organic layer was separated and concentrated down on a rotary evaporator to yield dark slush which solidified upon cooling. The solid was recrystallized from a mixture of isopropanol (650 mL) and water (35 mL) to give 512.1 g (78% yield) of bis(2,6-dimethyl-4-tert-butylphenyl)disulfide (formula III, Table 3), shown to be clean by TLC and NMR. $^1$H NMR (CDCl$_3$) δ 7.02 (s, 4H, Ar—H), 2.21 (s, 12H, CH$_3$), 1.29 (s, 18H, C(CH$_3$)$_3$).

The present example illustrates the utility of the present invention for synthesizing intermediates for producing fluorinating agents that can be used to produce fluorine-containing compounds.

Example 1b

Preparation of bis(2,6-dimethyl-3-chloro-4-tert-butylphenyl)disulfide

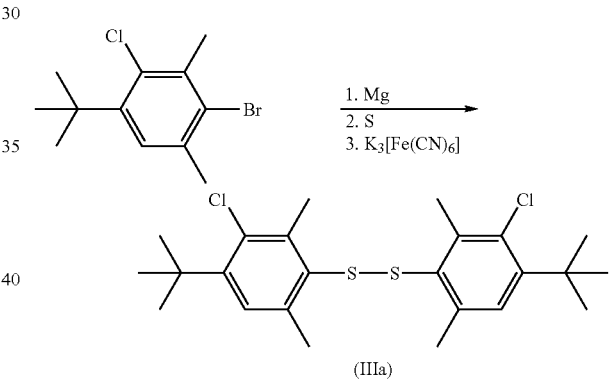

In a three neck dry flask equipped with a water condenser, 33 g (0.12 mol) of 2,6-dimethyl-3-chloro-4-tert-butylphenyl bromide, and 2.8 g (0.12 mol) of magnesium were mixed in anhydrous THF (200 ml). A catalytic amount of iodine was added and the mixture was heated to 80° C. The mixture was refluxed 2 h and cooled on an ice bath. Sulfur powder 3.8 g, (0.12 mole) was added portion wise. The mixture was heated to 80° C. for 2 h and cooled on an ice bath. A solution of potassium hexacyanoferrate, 239.48 g (0.12 mol) in water (300 mL) was added. After mixing well, product was extracted with ether (200 mL). The ether extract was dried over anhydrous magnesium sulfate and filtered. Removal of solvent at reduced pressure gave a viscous solid which was crystallized from ethanol to give 13.6 g (50%) of bis(2,6-dimethyl-3-chloro-4-tert-butylphenyl)disulfide (formula IIIa, Table 3): Mp 128-129° C.; $^1$H NMR (CDCl$_3$) δ 1.49 (s, 18H, C(CH$_3$)$_3$), 2.245 (s, 6H, CH$_3$), 2.252 (s, 6H, CH$_3$) 7.14 (s, 2H, Ar—H).

The present example illustrates the utility of the present invention for synthesizing intermediates for producing fluorinating agents that can be used to produce fluorine-containing compounds.

Example 1c

Preparation of bis(2,6-dimethyl-3-chloro-4-tert-butylphenyl)disulfide

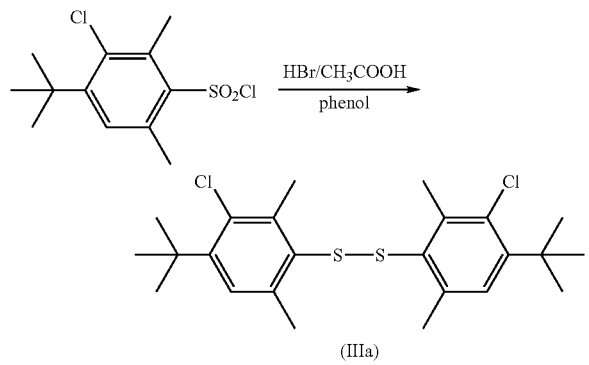

(IIIa)

In a flask, 15.6 g (53 mmol) of 2,6-dimethyl-3-chloro-4-tert-butylbenzenesulfonyl chloride, 6.0 g (64 mmol) of phenol and 20 mL of glacial acetic acid were placed. The flask was heated on a bath of 35° C. Approximately 30 mL (165 mmol of HBr) of 33 wt % hydrogen bromide/acetic acid solution was added to the flask. The reaction mixture was slowly heated at 60° C. A strong acidic gas evolved from the reaction mixture. The reaction mixture was stirred at 60° C. for 4.5 hours and cooled to room temperature. Into the reaction mixture, 250 mL of water was added, and the reaction mixture was filtered to give precipitates. The precipitates were washed with water. The obtained precipitates were added to 100 mL of isopropanol and the mixture stirred, the precipitates were collected by filtration to give 10.3 g (86%) of bis(2,6-dimethyl-3,5-dichloro-4-tert-butylphenyl)disulfide (formula IIIa, Table 3). The spectral data were in good agreement with the data in Example 1b.

The present example illustrates the utility of the present invention for synthesizing intermediates for producing fluorinating agents that can be used to produce fluorine-containing compounds.

Example 1d

Preparation of bis(2,6-dimethyl-3,5-dichloro-4-tert-butylphenyl)disulfide

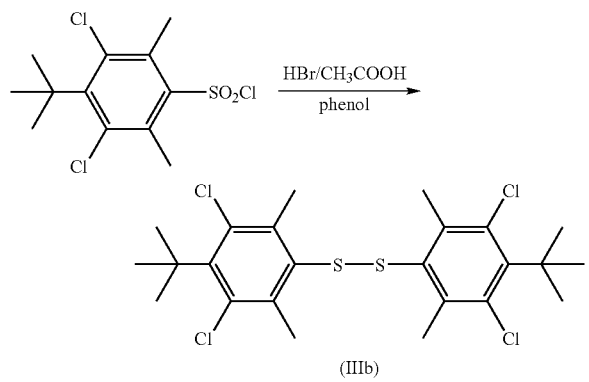

(IIIb)

Using a synthesis procedure similar to the one described in Example 1c, bis(2,6-dimethyl-3,5-dichloro-4-tert-butylphenyl)disulfide was prepared. However, unlike in Example 1c, 2,6-dimethyl-3,5-dichloro-4-tert-butylbenzenesulfonyl chloride was used instead of 2,6-dimethyl-3-chloro-4-tert-butylbenzenesulfonyl chloride.

The above described synthesis procedure produced 2,6-dimethyl-3,5-dichloro-4-tert-butylbenzenesulfonyl chloride (see Formula IIIb, Table 3). A yield of 73% was obtained. The physical and spectral data of the material are as follows: Mp 147.5-148.5° C. (recrystallized from $CH_2Cl_2$); $^1$H NMR ($CDCl_3$) δ 1.72 (s, 18H, $C(CH_3)_3$), 2.31 (s, 6H, $CH_3$). Elemental analysis: Calculated for $C_{24}H_{30}O_4S_2$: C, 54.97%; H, 5.77%. Found: C, 55.02%; H, 5.81%.

The present example illustrates the utility of the present invention for synthesizing intermediates for producing fluorinating agents that can be used to produce fluorine-containing compounds.

Example 1e

Preparation of bis[2,6-bis(methoxymethyl)phenyl]disulfide

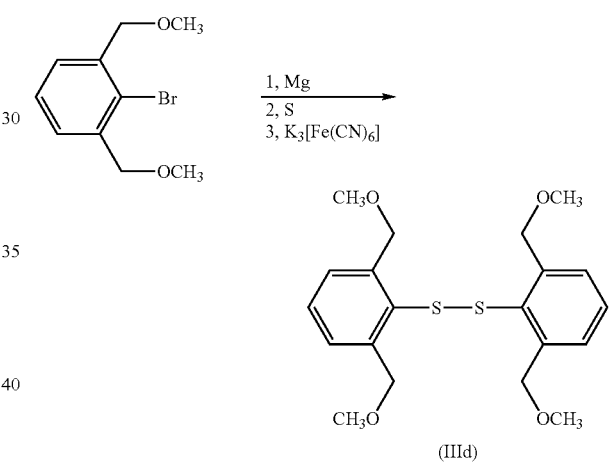

(IIId)

In a three neck dry flask equipped with a water condenser, 15 g (0.061 mol) of 1-bromo-2,6-bis(methoxymethyl)benzene and 1.7 g (0.07 mol) of magnesium were mixed in anhydrous THF (200 mL). A catalytic amount of iodine was added and the mixture was heated to reflux. After refluxing for 2 hours the reaction was cooled on an ice bath and sulfur was added pinch wise. The mixture was refluxed for 2 additional hours and cooled on an ice bath. A solution of potassium hexacyanoferrate, 2.0 g (0.07 mol) in water (200 mL) was added. After mixing well, product was extracted with ether (200 mL). The ether extract was dried over anhydrous magnesium sulfate and filtered. Removal of solvent at reduced pressure gave viscous solid which was crystallized from ethanol to give 8.3 g (65%) of bis[2,6-bis(methoxymethyl)phenyl]disulfide (formula IIId, Table 3): Mp 89-90° C.; $^1$H-NMR ($CDCl_3$) δ 3.27 (s, 6H, $OCH_3$), 4.36 (br.s, 4H, $CH_2$), 7.39 (s, 3H, Ar—H). Elemental analysis: Calculated for $C_{20}H_{26}O_4S_2$: C, 60.88%; H, 6.64%. Found: C, 60.56%; H, 6.64%.

The present example illustrates the utility of the present invention for synthesizing intermediates for producing fluorinating agents that can be used to produce fluorine-containing compounds.

Example 1f

Preparation of bis[2,6-di(methoxymethyl)-4-tert-butylphenyl]disulfide

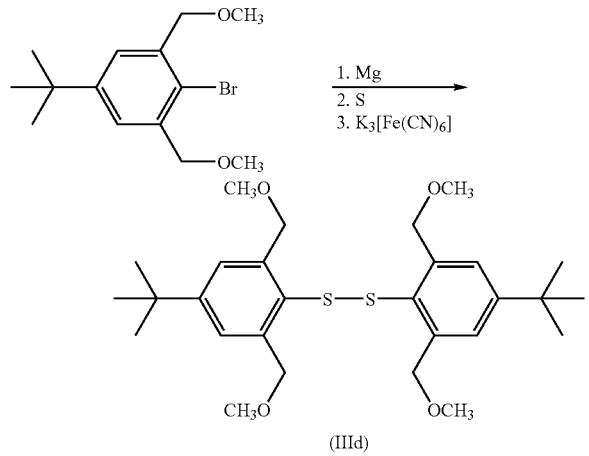

(IIId)

Using a synthesis procedure similar to the one described in Example 1e, bis[2,6-bis(methoxymethyl)-4-tert-butylphenyl]disulfide was prepared. However, unlike in Example 1e, 1-bromo-2,6-bis(methoxymethyl)-4-tert-butylbenzene was used instead of 1-bromo-2,6-bis(methoxymethyl)benzene.

The above described synthesis procedure produced bis[2,6-bis(methoxymethyl)-4-tert-butylphenyl]disulfide (see Formula IIId, Table 3). A yield of 65% was obtained. The physical and spectral data of the material are as follows: Mp 94-95° C. (recrystallized from ethanol); $^1$H-NMR (CDCl$_3$) δ 1.32 (s, 9H, C(CH$_3$)$_3$), 3.25 (s, 6H, OCH$_3$), 4.37 (br.s, 4H, CH$_2$), 7.41 (s, 2H, Ar—H); $^{13}$C-NMR (CDCl$_3$) δ 31.3, 35.1, 58.4, 72.5, 124.0, 128.6, 142.4, 153.7.

The present example illustrates the utility of the present invention for synthesizing intermediates for producing fluorinating agents that can be used to produce fluorine-containing compounds.

Example 1g

Preparation of bis[2,6-bis(ethoxymethyl)-4-tert-butylphenyl]disulfide

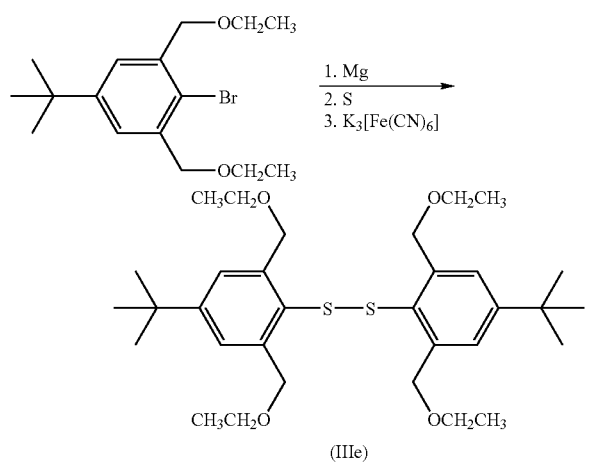

(IIIe)

Using a synthesis procedure similar to the one described in Example 1e, bis[2,6-bis(ethoxymethyl)-4-tert-butylphenyl]disulfide was prepared. However, unlike in Example 1e, 1-bromo-2,6-bis(ethoxymethyl)-4-tert-butylbenzene was used instead of 1-bromo-2,6-bis(methoxymethyl)benzene.

The above described synthesis procedure produced bis[2,6-bis(ethoxymethyl)-4-tert-butylphenyl]disulfide (see Formula IIIe, Table 3). A yield of 66% was obtained. The physical and spectral data of the material are as follows: Mp 62-63° C. (recrystallized from methanol); $^1$H-NMR (CDCl$_3$) δ 1.18 (t, 12H, CH$_2$CH$_3$), 1.31 (s, 9H, C(CH$_3$)$_3$), 3.38 (q, 8H, OCH$_2$), 4.40 (br.s, 8H, CH$_2$), 7.42 (s, 2H, Ar—H); $^{13}$C,NMR (CDCl$_3$) δ 15.34, 31.31, 35.04, 66.05, 70.52, 124.03, 128.93, 142.78, 153.57. Elemental analysis: Calcd for C$_{32}$H$_{50}$O$_4$S$_2$: C, 68.28%; H, 8.95%. Found: C, 68.30%; H, 8.83%.

The present example illustrates the utility of the present invention for synthesizing intermediates for producing fluorinating agents that can be used to produce fluorine-containing compounds.

Example 1h

Preparation of bis[2,6-bis(isopropoxymethyl)-4-tert-butylphenyl]disulfide

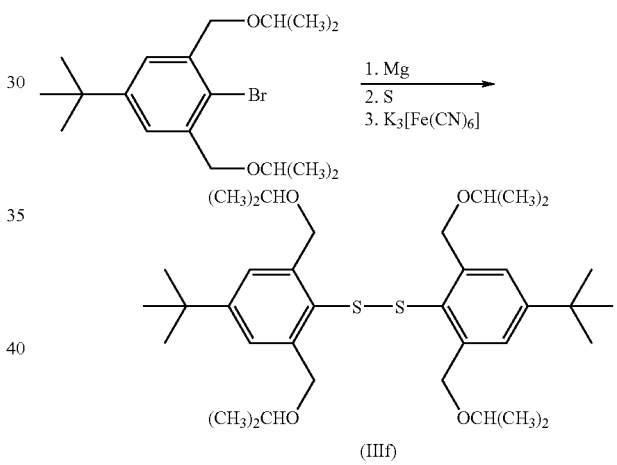

(IIIf)

Using a synthesis procedure similar to the one described in Example 1e, bis[2,6-bis(isopropoxymethyl)-4-tert-butylphenyl]disulfide was prepared. However, unlike in Example 1e, 1-bromo-2,6-bis(isopropoxymethyl)-4-tert-butylbenzene was used instead of 1-bromo-2,6-bis(methoxymethyl)benzene and the product (IIIf) was purified by column-chromatography using a 3:97 mixture of ethyl acetate and hexane as an eluent.

The above described synthesis procedure produced bis[2,6-bis(isopropoxymethyl)-4-tert-butylphenyl]disulfide (see Formula IIIf, Table 3). A yield of 50% was obtained. The spectral data of the material are as follows: $^1$H NMR (CDCl$_3$) δ 1.12 (d, J=6 Hz, 24H, CH$_3$), 1.31 (s, 18H, C(CH$_3$)$_3$), 3.48 (septet, J=6.0 Hz, 4H, CH), 4.39 (br.s, 8H, CH$_2$), 7.45 (s, 4H); $^{13}$C NMR (CDCl$_3$) δ 22.28, 31.30, 35.05, 68.22, 71.57, 124.30, 129.16, 143.14, 153.38.

The present example illustrates the utility of the present invention for synthesizing intermediates for producing fluorinating agents that can be used to produce fluorine-containing compounds.

Example 1i

Preparation of bis[2,6-bis(isobutoxymethyl)-4-tert-butylphenyl]disulfide

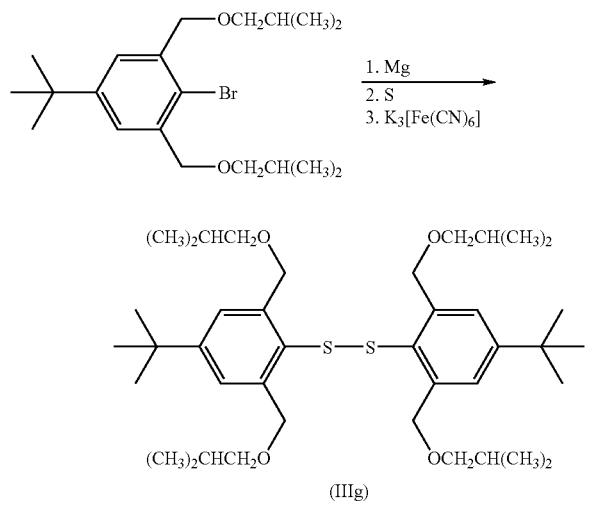

(IIIg)

Using a synthesis procedure similar to the one described in Example 1e, bis[2,6-bis(isobutoxymethyl)-4-tert-butylphenyl]disulfide was prepared. However, unlike in Example 1e, 4-tert-butyl-2,6-bis(isobutoxymethyl)-1-bromobenzene was used instead of 1-bromo-2,6-bis(methoxymethyl)benzene.

The above described synthesis procedure produced bis[2,6-bis(isobutoxymethyl)-4-tert-butylphenyl]disulfide (see Formula IIIg, Table 3). A yield of about 60% was obtained. The product was purified by thin-layered chromatography using a 3:97 (v/v) mixture of ethyl acetate and hexane as an eluent. The spectral data of the material are as follows: $^1$H NMR (CDCl$_3$) δ 0.91 (d, 24H, J=6 Hz, CH$_3$), 1.32 (s, 18H, C(CH$_3$)$_3$), 1.90 (m, 4H, CH(CH$_3$)$_2$), 4.40 (br.s, 8H, CH$_2$), 7.45 (s, 4H, Ar—H); $^{13}$C NMR (CDCl$_3$) δ 19.60, 28.62, 31.32, 35.06, 76.69, 77.64, 123.78, 128.70, 142.86, 153.50.

The present example illustrates the utility of the present invention for synthesizing intermediates for producing fluorinating agents that can be used to produce fluorine-containing compounds.

Example 1j

Preparation of bis[2,6-bis(tert-butoxymethyl)-4-tert-butylphenyl]disulfide

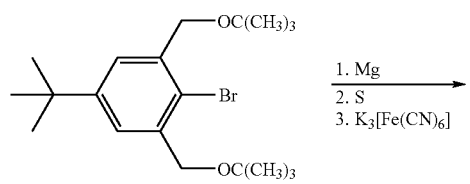

(IIIh)

Using a synthesis procedure similar to the one described in Example 1e, bis[2,6-bis(tert-butoxymethyl)-4-tert-butylphenyl]disulfide was prepared. However, unlike in Example 1e, 1-bromo-2,6-bis(tert-butoxymethyl)-4-tert-butylbenzene was used instead of 1-bromo-2,6-bis(methoxymethyl)benzene.

The above described synthesis procedure produced bis[2,6-bis(tert-butoxymethyl)-4-tert-butylphenyl]disulfide (see Formula IIIh, Table 3). A yield of 80% was obtained. The physical and spectral data of the material are as follows: Mp 120-121° C. (recrystallized from methanol); $^1$H NMR (CDCl$_3$) δ 1.15 (s, 36H), 1.31 (s, 18H), 4.38 (br.s, 8H), 7.47 (s, 4H); $^{13}$C NMR (CDCl$_3$) δ 27.82, 31.34, 35.07, 62.28, 73.53, 124.10, 128.32, 143.84. Elemental analysis: Calcd for C$_{40}$H$_{66}$O$_4$S$_2$: C, 71.17%; H, 9.85%. Found: C, 71.25%; H, 9.84%.

The present example illustrates the utility of the present invention for synthesizing intermediates for producing fluorinating agents that can be used to produce fluorine-containing compounds.

Example 2

Synthesis Embodiment of 2,6-dimethyl-4-tert-butylphenylsulfur trifluoride

A Fluorinating Agent of the Present Invention

The following reaction scheme is provided as illustrative for this example:

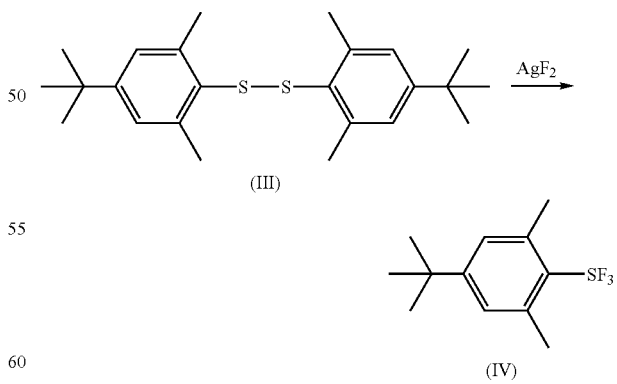

A 100 ml fluoropolymer (PFA)-round flask equipped with a magnetic stirrer, a thermometer and a solid addition funnel connected to a drying tube, was flushed with dry nitrogen and charged with 16.08 grams (g) (111 mmol) of silver difluoride and 20 ml of anhydrous 1,1,2-trichlorotrifluoroethane. Bis(2,6-dimethyl-4-tert-butylphenyl)disulfide (6.03 g, 16.3 mmol), charged in the solid addition funnel, was added to the stirred slurry in small portions to maintain the temperature of reaction mixture between 35° and 40° C. The addition of disulfide required approximately twenty minutes.

The reaction mixture was stirred for an additional thirty minutes at room temperature, and then heated to reflux for about five minutes. The reaction mixture was filtered under a blanket of dry nitrogen. After the evaporation of the solvent, the residue was distilled at reduced pressure to give 2,6-dimethyl-4-tert-butylphenylsulfur trifluoride shown as formula (IV), Table 4 (bp 92-93° C./0.5 mmHg, mp 59.1° C. (by DSC)). The compound was a white solid, yield of 5.20 g (64%).

The spectral data of the material is as follows: $^{19}$F NMR (THF-$d_8$) δ 53.90 (d, J=60.7 Hz, 2F), −57.03 (t, J=60.7 Hz, 1F); $^1$H NMR (CD$_3$CN) δ 7.25 (s, 2H), 2.60 (s, 6H), 1.30 (s, 9H); $^{13}$C NMR (CD$_3$CN) δ 155.37 (s), 141.61 (s), 133.74 (s), 127.56 (s), 34.45 (s), 30.25 (s), 19.09 (s); MS (EI) m/z 149.0 (M$^+$+1-2F, 100.0), 250.1 (M$^+$, 1.8); HRMS (EI) for C$_9$H$_{11}$F$_3$S (M$^+$): found 250.101491, calcd 250.100307.

The present example illustrates the utility of the present invention for synthesizing fluorinating agents that can be used to produce fluorine-containing compounds.

Example 3

Synthesis Embodiment of 2,6-dimethyl-4-tert-butylphenylsulfur trifluoride

A Fluorinating Agent of the Present Invention

The following reaction scheme is provided as illustrative for this example:

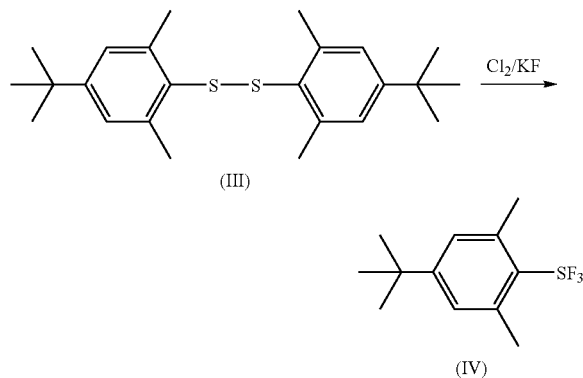

Chlorine (Cl$_2$) was passed at 23 ml/min through a stirred mixture of 5.79 g (15.0 mmol) of bis(2,6-dimethyl-4-tert-butylphenyl)disulfide and 8.7 g (58.1 mmol) of spray-dried potassium fluoride (KF) in 30 ml of dry acetonitrile cooled on an ice bath. After 1.18 L (52.5 mmol) of chlorine was passed, nitrogen was passed through at the rate of 25 ml/min for two hours. The reaction mixture was filtered in a dry atmosphere. The filtrate was evaporated under vacuum (10-20 mmHg) at 20° C. and the residue distilled at reduced pressure to give 2,6-dimethyl-4-tert-butylphenylsulfur trifluoride (see Formula IV, Table 4) (bp 68-70° C./0.1 mmHg (4.1 g, 55% yield, purity of >97.4%)). Spectral data was the same as shown in Example 2.

The present example illustrates the utility of the present invention for synthesizing fluorinating agents that can be used to produce fluorine-containing compounds.

Example 3a

Synthesis Embodiment of a mixture of 2,6-dimethyl-4-tert-butylphenylsulfur trifluoride and 2,6-dimethyl-3-chloro-4-tert-butylphenylsulfur trifluoride Fluorinating Agents of the Present Invention

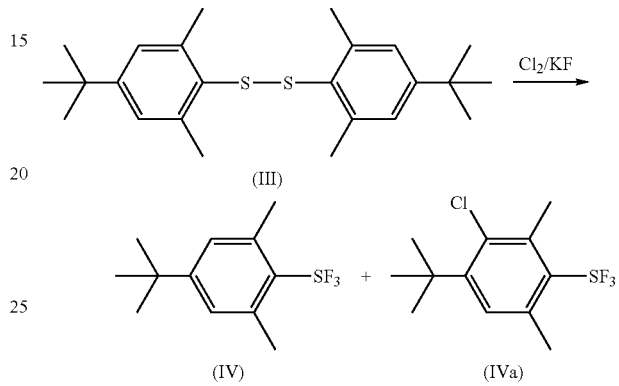

A 2000 mL fluoropolymer (PFA) vessel was charged with 40 g bis[2,6-dimethyl-4-tert-butylphenyl]disulfide (0.104 mol) and 60 g dry potassium fluoride (1.04 mol, dried under vacuum at 250° C. for three days) in a dry box. The vessel was taken out from the dry box and connected with the gas flow system. N$_2$ was passed through the vessel for about 30 minutes at a rate of 64 mL/min. Approximately 200 mL dry CH$_3$CN was then added to the mixture and the mixture allowed to cool on a bath of around −10° C. with N$_2$ flow continuing (64 mL/min). The reaction mixture was then bubbled with Cl$_2$ at the rate of 55 mL/min. The Cl$_2$ bubbling was stopped after 148 min (8154 mL of Cl$_2$ (0.364 mol) was bubbled). The reaction mixture changed from light yellow, to orange, and then to pale yellow. The reaction mixture was slowly warmed to room temperature with N$_2$ flow (16 mL/min), and stirred overnight. Then, the reaction mixture was brought to the dry box and filtered. The filtrate was dried under vacuum to yield a light yellow solid. Distillation under vacuum (~0.4 mmHg, 120~130° C. for oil bath) yielded 43 g of the products, which were found by the NMR analysis to be a 93:7 (mol ratio) mixture of 2,6-dimethyl-4-tert-butylphenylsulfur trifluoride (formula IV, Table 3) and 2,6-dimethyl-3-chloro-4-tert-butylphenylsulfur trifluoride (formula IVa, Table 3).

2,6-dimethyl-4-tert-butylphenylsulfur trifluoride: Yield 76%; $^1$H NMR (CD$_3$CN/Et$_2$O (1/1, v/v)), 7.29 (s, 1H, Ar—H), 7.25 (s, 1H, Ar—H), 2.69 (d, J=5.5 Hz, 3H, CH$_3$), 2.57 (br.s, 3H, CH$_3$), 1.33 (s, 9H, C(CH$_3$)$_3$); $^{19}$F NMR (CD$_3$CN/Et$_2$O (1/1, v/v)), 53.2 (d, J=67 Hz, 2F, SF$_2$), −57.5 (t, J=67 Hz, 1F, SF).

2,6-dimethyl-3-chloro-4-tert-butylphenylsulfur trifluoride: Yield 5.7%; $^1$H NMR (CD$_3$CN/Et$_2$O=1/1, (v/v)), 7.39 (s, 1H, Ar—H), the CH$_3$ protons of the minor product were overlapped by the CH$_3$ protons of the main product, 1.52 (s, 9H, C(CH$_3$)$_3$); $^{19}$F NMR (CD$_3$CN/Et$_2$O (1/1, v/v)), 54.2 (d, J=63 Hz, 1.6F, SF$_2$), 53.6 (d, J=56 Hz, 0.4F, SF$_2$), −53.4 (t, J=56 Hz, 0.2F, SF), −56.0 (t, J=63 Hz, 0.4F, SF).

The present example illustrates the utility of the present invention for synthesizing fluorinating agents that can be used to produce fluorine-containing compounds.

Example 3b

Synthesis Embodiment of 2,6-dimethyl-3-chloro-4-tert-butylphenylsulfur trifluoride A Fluorinating Agent of the Present Invention

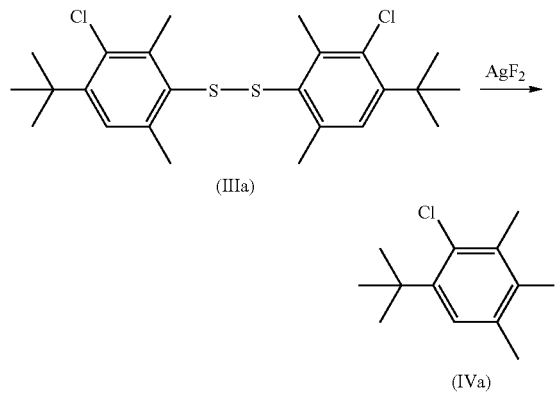

In a 100 mL fluoropolymer flask equipped with a magnetic stirring bar and a fluoropolymer condenser, 4.89 g (0.01 mol) of bis(2,6-dimethyl-3-chloro-4-tert-butylphenyl) disulfide was suspended in 20 mL of anhydrous 1,1,2-trichlorotrifluoroethane under nitrogen atmosphere. $AgF_2$ (9.92 g, 0.13 mol) was added in portion wise. The reaction started and heat was generated during addition of the $AgF_2$. After complete addition of $AgF_2$, the reaction was heated to 40° C. for 5 min and then stirred at room temperature for 0.5 h. All black powder of $AgF_2$ changed to yellow colored powder (AgF). Under nitrogen atmosphere, the solution was transferred to a 50 mL glass distillation flask, the yellow powder was washed with 15 mL of anhydrous 1,1,2-trichlorotrifluoroethane. Distillation at reduced pressure gave 4.7 g of 2,6-dimethyl-3-chloro-4-tert-butylphenylsulfur trifluoride (formula IVa, Table 3): Yield: 4.7 g (78%); bp 105-106° C./0.4 mmHg (bath temperature 125° C.); $^1H$ NMR (CDCl$_3$) δ 1.50 (s, 9H, C(CH$_3$)$_3$), 2.67 (s, 6H, CH$_3$), 7.23 (s, 1H, Ar—H); $^{19}F$ NMR (THF-d$_8$) δ 49.95 (1.6F, d, J=63 Hz, SF$_2$), 47.45 (0.4F, d, J=54 Hz, SF$_2$), −59.68 (0.4F, t, J=54 Hz, SF), −60.27 (1.6F, t, J=63 Hz, SF); $^{13}C$ NMR (CDCl$_3$) δ 18.00, 32.37, 41.28, 131.90, 135.84, 144.85, 148.67.

The present example illustrates the utility of the present invention for synthesizing fluorinating agents that can be used to produce fluorine-containing compounds.

Experiment 3c

Synthesis Embodiment of 2,6-dimethyl-3,5-dichloro-4-tert-butylphenylsulfur trifluoride A Fluorinating Agent of the Present Invention

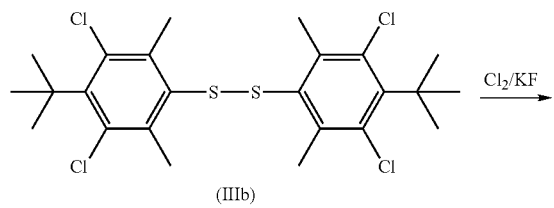

-continued

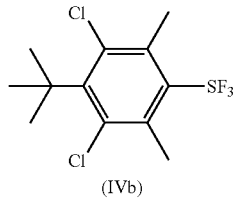

A fluoropolymer flask was charged with 5.24 g (0.01 mol) of bis(2,6-dimethyl-3,5-dichloro-4-tert-butylphenyl)disulfide, 5.8 g (0.1 mol) of dry potassium fluoride and 30 ml of anhydrous acetonitrile. Chlorine gas (0.035 mol, 784 mL) was bubbled through the mixture at a rate of 20 mL/min at ice water temperature. The ice bath was removed and the reaction mixture stirred at room temperature for 2 h. The reaction mixture was filtered and acetonitrile removed at reduced pressure. Distillation of the product at reduced pressure gave 5.05 g (80%) of 2,6-dimethyl-3,5-dichloro-4-tert-butylphenylsulfur trifluoride (see formula IVb, Table 3) as a colorless liquid: Bp 113-115° C./0.4 mmHg (bath temperature 130° C.); $^1H$ NMR (CDCl$_3$) δ 1.73 (s, 9H, C(CH$_3$)$_3$), 2.69 (s, 6H, CH$_3$); $^{19}F$ NMR (CDCl$_3$) δ 53.80 (br.s, 2F, SF$_2$), −51.49 (br.s, 1F, SF); $^{13}C$ NMR (CDCl$_3$) δ 18.00, 32.37, 41.28, 131.90, 135.84, 144.85, 148.67.

The present example illustrates the utility of the present invention for synthesizing fluorinating agents that can be used to produce fluorine-containing compounds.

Example 4

Synthesis Embodiment of 4-tert-butylphenylsulfur trifluoride

A Fluorinating Agent of the Present Invention

The following reaction scheme is provided as illustrative for this example:

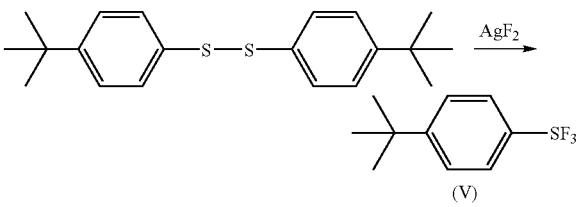

Using a synthesis procedure similar to the one described in Example 2, 4-tert-butylphenylsulfur trifluoride was prepared. However, unlike in Example 2, bis(4-tert-butylphenyl)disulfide was added to the slurry instead of the bis(2,6-dimethyl-4-tert-butylphenyl)disulfide.

The above described synthesis procedure produced 4-tert-butylphenylsulfur trifluoride (see Formula V, Table 3). The physical and spectral data of the material are as follows: Bp 76° C./1 mmHg; $^{19}F$ NMR (CD$_3$CN) δ 56.57 (br.s, 2F), −39.24 (br.s, 1F); $^1H$ NMR (CD$_3$CN) δ 7.95 (d, J=8.3 Hz, 2H), 7.67 (d, J=8.3 Hz, 2H), 1.33 (s, 9H); $^{13}C$ NMR (CD$_3$CN) δ 158.17 (s), 143.11 (s), 126.46 (s), 124.24 (s), 35.07 (s), 30.31 (s); MS (EI) m/z 222.1 (M$^+$, 0.4), 203.1 (M$^+$-F, 8.8), 137.1 (M$^+$-SF$_2$—CH$_3$, 100.0); HRMS (EI) for C$_{10}$H$_{13}$F$_3$S (M$^+$): found 222.068288, calcd 222.069007.

The present example illustrates the utility of the present invention for synthesizing fluorinating agents that can be used to produce fluorine-containing compounds.

Example 5

Synthesis Embodiment of 4-tert-butylphenylsulfur trifluoride

A Fluorinating Agent of the Present Invention

The following reaction scheme is provided as illustrative for this example:

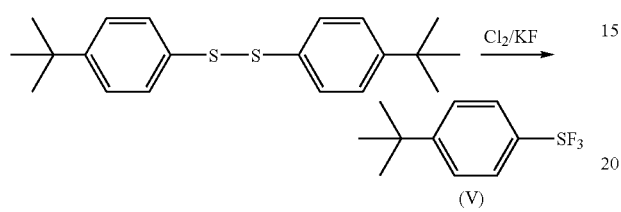

(V)

Using a synthesis procedure similar to the one described in Example 3, 4-tert-butylphenylsulfur trifluoride was prepared. However, unlike in Example 3, bis(4-tert-butylphenyl)disulfide was used as a starting material. A yield of 67% was obtained.

The physical and spectral data for the product produced in this Example was the same as shown in Example 4.

The present example illustrates the utility of the present invention for synthesizing fluorinating agents that can be used to produce fluorine-containing compounds.

Example 6

Synthesis Embodiment of 2,4,6-trimethylphenylsulfur trifluoride

A Fluorinating Agent of the Present Invention

The following reaction scheme is provided as illustrative for this example:

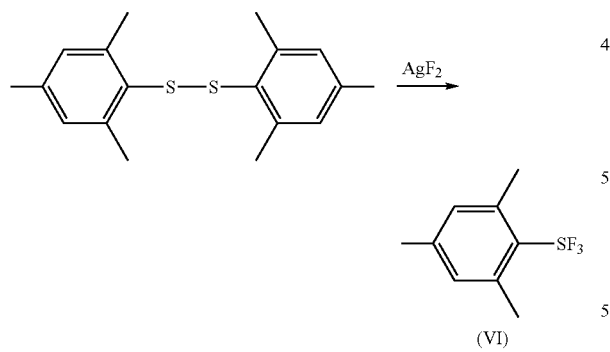

(VI)

Using a synthesis procedure similar to the one described in Example 2, 2,4,6-trimethylphenylsulfur trifluoride was prepared. However, unlike in Example 2, bis(2,4,6-trimethylphenyl)disulfide was added to the slurry instead of the bis(2,6-dimethyl-4-tert-butylphenyl)disulfide.

The above described synthesis procedure produced 2,4,6-trimethylphenylsulfur trifluoride (see Formula VI, Table 3). The physical and spectral data of the material are as follows: Bp 58-59° C./1 mmHg; $^{19}$F NMR (THF-$d_8$) δ 53.13 (d, J=52.0 Hz, 2F), −57.40 (t, J=43.4 Hz, 1F); $^1$H NMR (CD$_3$CN/THF-$d_8$) δ 6.97 (s, 1H), 6.94 (s, 1H), 2.59 (s, 3H), 2.47 (s, 3H), 2.24 (s); $^{13}$C NMR (THF-$d_8$) δ 142.33 (s), 141.83 (s), 134.20 (s), 133.03 (s), 130.86 (s), 129.99 (s), 20.07 (s), 18.83 (s), 18.70 (s); MS (EI) m/z 208.0 (M$^+$, 5.0), 189.0 (M$^+$-F, 15.4), 138.0 (M$^+$-SF$_2$, 100.0); HRMS (EI) for C$_9$H$_{11}$F$_3$S (M$^+$): found 208.052377, calcd 208.053357.

The present example illustrates the utility of the present invention for synthesizing fluorinating agents that can be used to produce fluorine-containing compounds.

Example 7

Synthesis Embodiment of 2,4,6-trimethylphenylsulfur trifluoride

A Fluorinating Agent of the Present Invention

The following reaction scheme is provided as illustrative for this example:

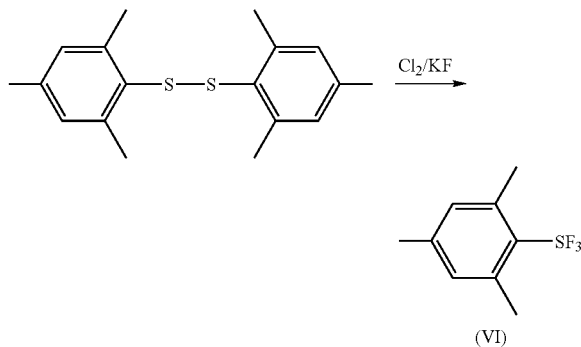

(VI)

Using a synthesis procedure similar to the one described in Example 3, 2,4,6-trimethylphenylsulfur trifluoride was prepared. However, unlike in Example 2, bis(2,4,6-trimethylphenyl)disulfide was used as a starting material. A yield of 58% was obtained.

The physical and spectral data for the product produced in this Example was the same as shown in Example 6.

The present example illustrates the utility of the present invention for synthesizing fluorinating agents that can be used to produce fluorine-containing compounds.

Example 8

Synthesis Embodiment of 2,4-dimethylphenylsulfur trifluoride

A Fluorinating Agent of the Present Invention

The following reaction scheme is provided as illustrative for this example:

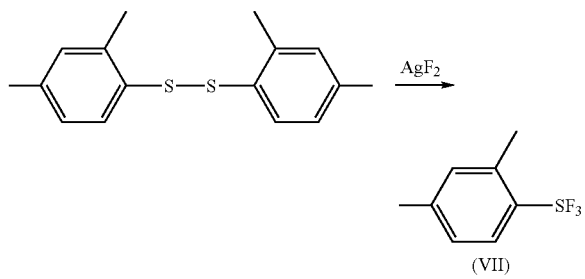

(VII)

Using a synthesis procedure similar to the one described in Example 2, 2,4-dimethylphenylsulfur trifluoride was prepared. However, unlike in Example 2, bis(2,4-dimethylphenyl)disulfide was added to the slurry instead of the bis(2,6-dimethyl-4-tert-butylphenyl)disulfide. A yield of 59% was obtained.

The above described synthesis procedure produced 2,4-dimethylphenylsulfur trifluoride (see Formula VII, Table 3). The physical and spectral data of the material are as follows: Bp 56° C./1 mmHg; $^{19}$F NMR (CD$_3$CN/THF-d$_8$) δ 52.44 (d, J=60.7 Hz, 2F), −57.75 (t, J=60.7 Hz, 1F); $^1$H NMR (CD$_3$CN) δ 7.90 (d, J=8.2 Hz, 1H), 7.29 (d, J=8.2 Hz, 1H), 7.18 (s, 1H), 2.62 (s, 3H), 2.42 (s, 3H); $^{13}$C NMR (CD$_3$CN/THF-d$_8$) δ 144.76 (s), 134.30 (s), 133.80 (s), 131.92 (s), 131.70 (s), 129.79 (s), 19.09 (s), 18.92 (s); MS (EI) m/z 194.0 (M$^+$, 6.9), 175.0 (M$^+$-F, 22.4), 124.0 (M$^+$-SF$_2$, 100.0); HRMS (EI) for C$_8$H$_9$F$_3$S (M$^+$): found 194.036951, calcd 194.037707.

The present example illustrates the utility of the present invention for synthesizing fluorinating agents that can be used to produce fluorine-containing compounds.

Example 9

Synthesis Embodiment of 2,4-dimethylphenylsulfur trifluoride

A Fluorinating Agent of the Present Invention

The following reaction scheme is provided as illustrative for this example:

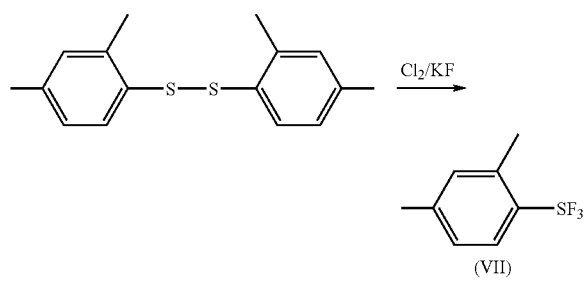

(VII)

Using a synthesis procedure similar to the one described in Example 3, 2,4-dimethylphenylsulfur trifluoride was prepared. However, unlike in Example 3, bis(2,4-dimethylphenyl)disulfide was used as a starting material. A yield of 71% was obtained.

The physical and spectral data for the product in this Example were the same as shown in Example 8.

The present example illustrates the utility of the present invention for synthesizing fluorinating agents that can be used to produce fluorine-containing compounds.

Example 10

Synthesis Embodiment of 2,5-dimethylphenylsulfur trifluoride

A Fluorinating Agent of the Present Invention

The following reaction scheme is provided as illustrative for this example:

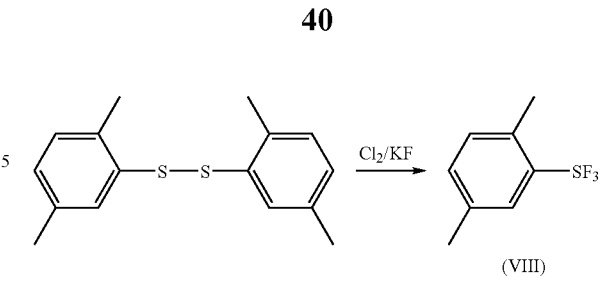

(VIII)

Using a synthesis procedure similar to the one described in Example 3, 2,5-dimethylphenylsulfur trifluoride was prepared. However, unlike in Example 3, bis(2,5-dimethylphenyl)disulfide was used as a starting material. A yield of 60% was obtained.

The above described synthesis procedure produced 2,5-dimethylphenylsulfur trifluoride (see Formula VIII, Table 3). The physical and spectral data of the material are as follows: Bp 76-79° C./3 mmHg; $^{19}$F NMR (CD$_3$CN) δ 60.89 (br.s, 2F), −57.15 (br, s, 1F); $^1$H NMR (CD$_3$CN) δ 7.90 (s, 1H), 7.36 (d, J=7.7 Hz, 1H), 7.26 (d, J=7.7 Hz, 1H), 2.66 (s, 3H), 2.49 (s, 3H); MS (EI) m/z 105.1 (M$^+$-SF$_3$, 100.0), 194.0 (M$^+$, 8.0); HRMS (EI) for C$_8$H$_9$F$_3$S (M$^+$): found 194.037412, calcd 194.037707.

The present example illustrates the utility of the present invention for synthesizing fluorinating agents that can be used to produce fluorine-containing compounds.

Example 11

Synthesis Embodiment of 2,6-dimethylphenylsulfur trifluoride

A Fluorinating Agent of the Present Invention

The following reaction scheme is provided as illustrative for this example:

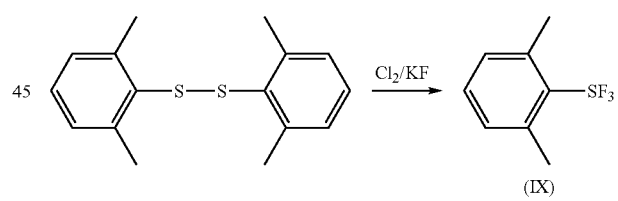

(IX)

Using a synthesis procedure similar to the one described in Example 3, 2,6-dimethylphenylsulfur trifluoride was prepared. However, unlike in Example 3, bis(2,6-dimethylphenyl)disulfide was used as a starting material. A yield of 75% was obtained.

The above described synthesis procedure produced 2,6-dimethylphenylsulfur trifluoride (see Formula IX, Table 3). The physical and spectral data of the material are as follows: Bp 73-75° C./3.5 mmHg; $^{19}$F NMR (CD$_3$CN) δ 53.51 (br.s, 2F), −55.99 (br.s, 1F); $^1$H NMR (CD$_3$CN) δ 7.41 (t, J=7.7 Hz, 1H), 7.23 (br.s, 2H), 2.86 (s, 3H), 2.70 (s, 3H); MS (EI) m/z 105.1 (M$^+$-SF$_3$, 100.0), 194.0 (M$^+$, 7.0); HRMS (EI) for C$_8$H$_9$F$_3$S (M$^+$): found 194.037035, calcd 194.037707.

The present example illustrates the utility of the present invention for synthesizing fluorinating agents that can be used to produce fluorine-containing compounds.

Example 12

Synthesis Embodiment of 4-fluorophenylsulfur trifluoride

A Fluorinating Agent of the Present Invention

The following reaction scheme is provided as illustrative for this example:

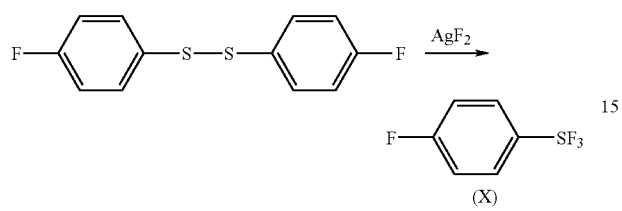

(X)

Using a synthesis procedure similar to the one described in Example 2, 4-fluorophenylsulfur trifluoride was prepared. However, unlike in Example 2, bis(4-fluorophenyl)disulfide was used as a starting material. A yield of 56% was obtained.

The above described synthesis procedure produced 4-fluorophenylsulfur trifluoride (see Formula X, Table 3). The physical and spectral data of the material are as follows: Bp 39-40° C./2 mmHg; $^{19}F$ NMR (CD$_3$CN/THF-d$_8$) δ 58.14 (d, J=60.7 Hz, 2F), −37.28 (t, J=32.0 Hz, 1F), −104.42 (s, 1F); $^1H$ NMR (CD$_3$CN/THF-d$_8$) δ 8.40 (dd, J=5.8, 8.6 Hz, 2H), 7.66 (t, J=8.6 Hz, 2H); $^{13}C$ NMR (CD$_3$CN/THF-d$_8$) δ 165.98 (d, J=255.0 Hz), 142.41 (d, J=15.2 Hz), 130.66 (d, J=8.0 Hz), 116.69 (d, J=23.1 Hz); MS (EI) m/z 184.0 (M$^+$-F, 0.1), 165.0 (M$^+$-F, 18.5), 114.0 (M$^+$-SF$_2$, 100.0); HRMS (EI) for C$_6$H$_4$F$_4$S (M$^+$): found 183.996675, calcd 183.996985.

The present example illustrates the utility of the present invention for synthesizing fluorinating agents that can be used to produce fluorine-containing compounds.

Example 13

Synthesis Embodiment of 4-chlorophenylsulfur trifluoride

A Fluorinating Agent of the Present Invention

The following reaction scheme is provided as illustrative for this example:

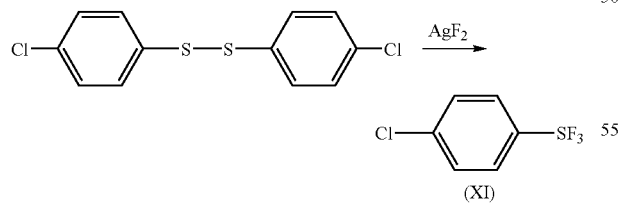

(XI)

Using a synthesis procedure similar to the one described in Example 2, 4-chlorophenylsulfur trifluoride was prepared. However, unlike in Example 2, bis(4-chlorophenyl) disulfide was used as a starting material. A yield of 32% was obtained.

The above described synthesis procedure produced 4-chlorophenylsulfur trifluoride (see Formula XI, Table 3). The physical and spectral data of the material are as follows: Bp 55-56° C./1 mmHg; $^{19}F$ NMR (CD$_3$CN/THF-d$_8$) δ 58.20 (d, J=60.7 Hz, 2F), −39.44 (t, J=60.7 Hz, 1F); $^1H$ NMR (CD$_3$CN/THF-d$_8$) δ 8.19 (d, J=7.6 Hz, 2H), 7.82 (d, J=7.6 Hz, 2H); $^{13}C$ NMR (CD$_3$CN) δ 144.65 (s), 140.00 (s), 129.56 (s), 128.38 (s); MS (EI) m/z 201.9 (M$^+$, 0.3), 199.9 (M$^+$, 0.9), 130.0 (M$^+$-SF$_2$, 100.0), HRMS (EI) for C$_6$H$_4$ClF$_3$S (M$^+$): found 201.965496, calcd. 201.964484, and found 199.967032, calcd 199.967434.

The present example illustrates the utility of the present invention for synthesizing fluorinating agents that can be used to produce fluorine-containing compounds.

Example 14

Synthesis Embodiment of 3-methyl-4-chlorophenylsulfur trifluoride, A Fluorinating Agent of the Present Invention The following reaction scheme is provided as illustrative for this example:

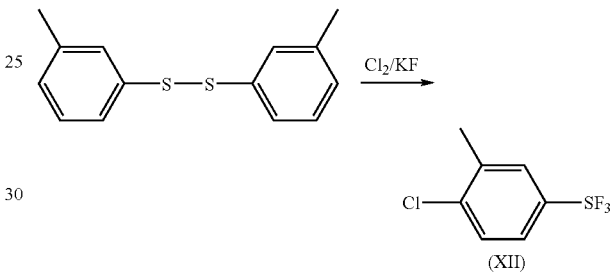

(XII)

Chlorine (Cl$_2$) was passed at a rate of 30 mL/min into a stirred mixture of 4.44 g (18 mmol) of bis(3-methylphenyl) disulfide and 15.7 g (270 mmol) of spray-dried KF. The stirred mixture also included 100 ml of dry acetonitrile. The mixture was stirred on an ice bath. After 1.92 L (85.7 mmol) of chlorine was passed through the mixture, nitrogen was then passed through the mixture for 3 hours at room temperature. The reaction mixture was then filtered in a dry atmosphere and the filtrate was evaporated under reduced pressure without heating.

Residue was distilled at reduced pressure to give 4.71 g of the compound as shown in Formula XII, Table 3. A yield of 61% was obtained. The physical and spectral data of the material are as follows: Bp 72-75° C./4 mmHg; $^{19}F$ NMR (CDCl$_3$) δ 57.9 (br.s, 2F), −37.7 (br.s, 1F); $^1H$ NMR (CDCl$_3$) δ 7.85 (br.s, 1H), 7.73 (d, J=8.6 Hz, 1H), 7.46 (d, J=8.6 Hz, 1H), 2.30 (s, 3H); MS (EI) m/z 125.0 (M$^+$-SF$_3$, 100.0), 214 (M$^+$, 1.2); HRMA (EI) for C$_7$H$_6$ClF$_3$S (M$^+$): found 215.980817, calcd 215.980134, and found 213.983426, calcd 213.983085.

The present example illustrates the utility of the present invention for synthesizing fluorinating agents that can be used to produce fluorine-containing compounds.

Example 15

Synthesis Embodiment of 2,4,6-tri(isopropyl)phenylsulfur trifluoride, A Fluorinating Agent of the Present Invention The following reaction scheme is provided as illustrative for this example:

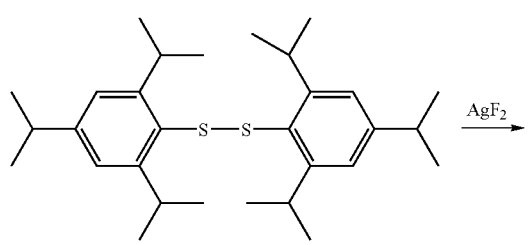

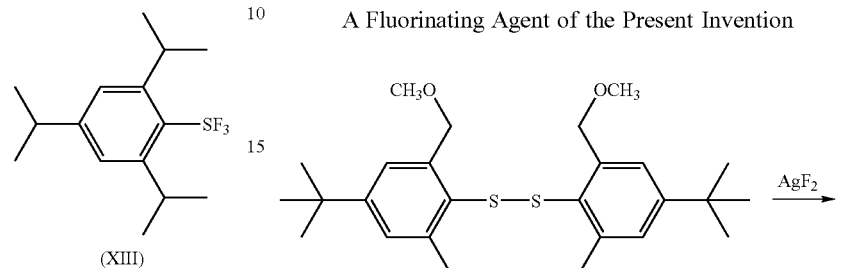

(XIII)

In a similar way as in Example 2, 2,4,6-tri(isopropyl)phenylsulfur trifluoride was synthesized from bis[2,4,6-tris(isopropyl)phenyl]disulfide. A yield of 79% was obtained. The purification of this compound was achieved by sublimation at 70° C./0.1 mmHg. The formula is shown as Formula XIII, Table 3.

The physical and spectral data of the material are shown in the following: Mp 87.3° C. (by DSC); $^{19}$F NMR (THF-$d_8$) δ 60.68 (d, J=52.0 Hz, 2F), −53.88 (t, J=52.0 Hz, 1F); $^1$H NMR (CD$_3$CN) δ 7.33 (s, 1H), 7.27 (s, 1H), 3.89 (m, 1H), 3.44 (m, 1H), 2.95 (septet, J=7.1 Hz, 1H), 1.29 (d, J=6.6 Hz, 12H), 1.24 (d, J=7.1 Hz, 6H); MS (EI) m/z 149.0 (M$^+$+1-2F, 100.0), 292.2 (M$^+$, 1.2); HRMS (EI) for C$_{15}$H$_{23}$F$_3$S (M$^+$): found 292.145944, calcd 292.147257.

The present example illustrates the utility of the present invention for synthesizing fluorinating agents that can be used to produce fluorine-containing compounds.

Example 15a

Synthesis Embodiment of 2,6-di(methoxymethyl)phenylsulfur trifluoride

A Fluorinating Agent of the Present Invention

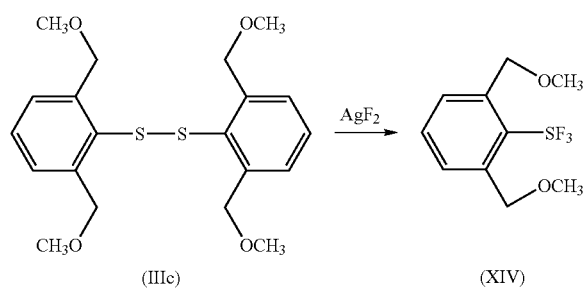

(IIIc)                                (XIV)

Using a synthesis procedure similar to the one described in Example 3b, 2,6-bis(methoxymethyl)phenylsulfur trifluoride (formula XIV, Table 3) was prepared. However, unlike Example 3b, bis[2,6-bis(methoxymethyl)phenyl]disulfide was used as a starting material. A yield of 77% was obtained. The physical and spectral data of the material are as follows: Bp 110° C./0.4 mmHg (bath temperature 130° C.); $^1$H NMR (CDCl$_3$) δ 3.41 (s, 6H, OCH$_3$), 4.83 (br.s, 4H, CH$_2$), 7.42 (m, 3H, Ar—H); $^{19}$F NMR (CDCl$_3$) δ 50.37 (br.s, 2F, SF$_2$), −53.1 (br.s, 1F, SF); $^{13}$C NMR (CDCl$_3$) δ 58.4, 71.7, 128.3, 131.4, 136.4, 144.6. Elemental analysis: Calcd for C$_{10}$H$_{13}$F$_3$O$_2$S: C, 47.24%; H, 5.15%. Found: C, 47.02%; H, 5.12%.

The present example illustrates the utility of the present invention for synthesizing fluorinating agents that can be used to produce fluorine-containing compounds.

Example 15b

Synthesis Embodiment of 2,6-bis(methoxymethyl)-4-tert-butylphenylsulfur trifluoride A Fluorinating Agent of the Present Invention

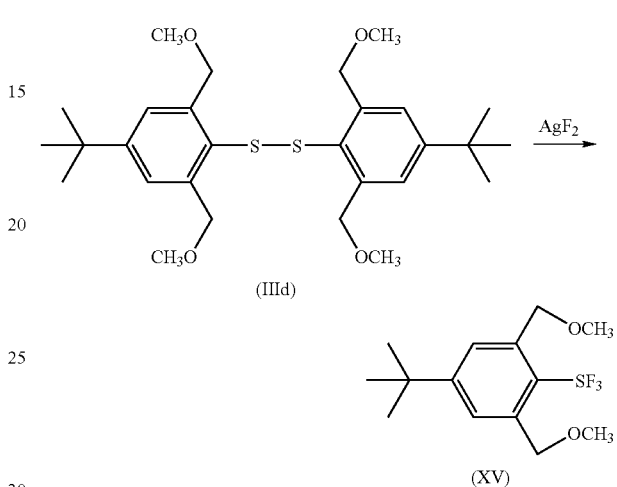

(IIId)

(XV)

Using a synthesis procedure similar to the one described in Example 3b, 2,6-bis(methoxymethyl)-4-tert-butylphenylsulfur trifluoride (formula XV, Table 3) was prepared. However, unlike Example 3b, bis[2,6-bis(methoxymethyl)-4-tert-butylphenyl]disulfide was used as a starting material. A yield of 75% was obtained. The physical and spectral data of the material are as follows: Bp 128-130° C./0.4 mmHg (bath temperature 150° C.); $^1$H NMR (CDCl$_3$) δ 1.34 (s, 9H, C(CH$_3$)$_3$), 3.46 (s, 6H, OCH$_3$), 4.82 (br.s, 4H, CH$_2$), 7.41 (s, 2H, Ar—H); $^{19}$F NMR (CDCl$_3$) δ 48.68 (br.s, 2F, SF$_2$), −53.37 (br.s, 1F, SF); $^{13}$C NMR (CDCl$_3$) δ 31.0, 35.1, 58.5, 76.7, 125.4, 136.2, 141.5, 155.0. Elemental analysis: Calcd for C$_{14}$H$_{21}$F$_3$O$_2$S: C, 54.18%; H, 6.82%. Found: C, 54.31%; H, 6.86%.

The present example illustrates the utility of the present invention for synthesizing fluorinating agents that can be used to produce fluorine-containing compounds.

Example 15c

Synthesis Embodiment of 2,6-bis(methoxymethyl)-4-tert-butylphenylsulfur trifluoride A Fluorinating Agent of the Present Invention

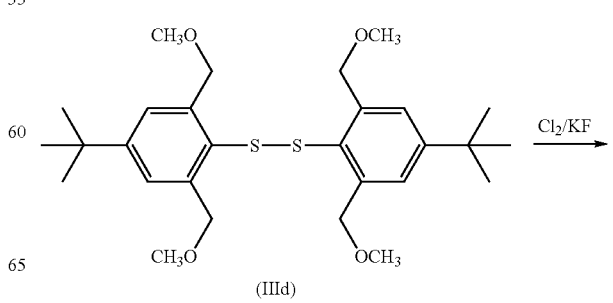

(IIId)

-continued

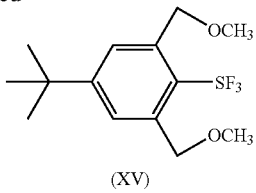

(XV)

A 500 mL fluoropolymer flask was charged with 22.4 g (0.044 mol) of bis[2,6-bis(methoxymethyl)-4-tert-butylphenyl]disulfide, 25.5 g (0.44 mol) of dry potassium fluoride and 100 mL of anhydrous acetonitrile. The mixture was cooled to 0° C. and chlorine gas (0.15 mol, 3360 mL) bubbled through at a rate of 35 mL/min. The reaction mixture was stirred at 0° C. for another 1 h, followed by stirring at room temperature for 1 h. The reaction mixture was filtered and acetonitrile removed at reduced pressure at room temperature. The resultant liquid was distilled at reduced pressure to give 24 g of 2,6-di(methoxymethyl)-4-tert-butylphenylsulfur trifluoride (formula XV, Table 3). Yield: 88%. The spectral data are as shown in Example 15b.

The present example illustrates the utility of the present invention for synthesizing fluorinating agents that can be used to produce fluorine-containing compounds.

Example 15d

Synthesis Embodiment of 2,6-bis(ethoxymethyl)-4-tert-butylphenylsulfur trifluoride A Fluorinating Agent of the Present Invention

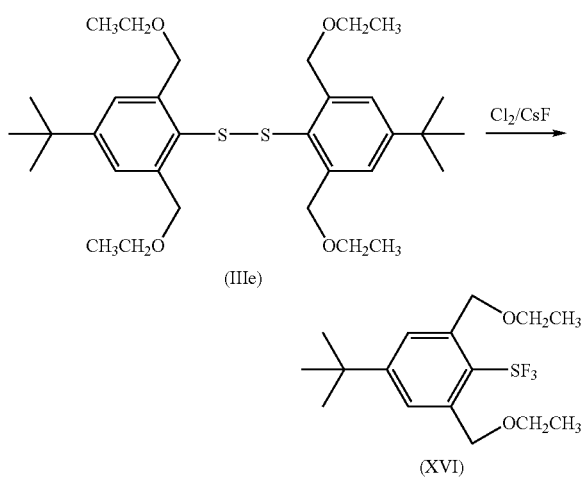

A fluoropolymer flask was charged with 3.14 g (6.0 mmol) of bis[2,6-bis(ethoxymethyl)-4-tert-butylphenyl]disulfide, 18.2 g (120 mmol) of dry cesium fluoride and 35 mL of anhydrous acetonitrile. Chlorine gas (16.00 mmol, 538 mL) was bubbled at the rate of 15 mL/min at 20° C. (water bath temperature). After passing chlorine, water bath was removed and mixture was stirred at room temperature for 1 hour. The solution was transferred by decantation under nitrogen atmosphere followed by washing with 15 mL of anhydrous acetonitrile. Acetonitrile was removed at room temperature and product was purified by distillation at reduced pressure to give 2.5 g (65%) of 2,6-bis(ethoxymethyl)-4-tert-butylphenylsulfur trifluoride (formula XVI, Table 3) as a light yellow liquid: Bp 118° C./0.2 mm (bath temperature=140° C.); $^1$H NMR (CDCl$_3$) δ 1.32 (6H, CH$_2$CH$_3$), 1.32 (s, 9H, C(CH$_3$)$_3$), 3.60 (q, 4H), 4.89 (s, 4H), 7.54 (s, 2H, Ar—H); $^{19}$F NMR (CDCl$_3$) δ 48.77 (br, s, 2F, SF$_2$), −53.11 (br.s, 1F, SF); $^{13}$C-NMR (CDCl$_3$) δ 15.12, 31.02, 35.05, 66.29, 66.48, 125.33, 136.71, 154.89, 156.97.

The present example illustrates the utility of the present invention for synthesizing fluorinating agents that can be used to produce fluorine-containing compounds.

Example 15e

Synthesis Embodiment of 2,6-bis(isopropoxymethyl)-4-tert-butylphenylsulfur trifluoride A Fluorinating Agent of the Present Invention

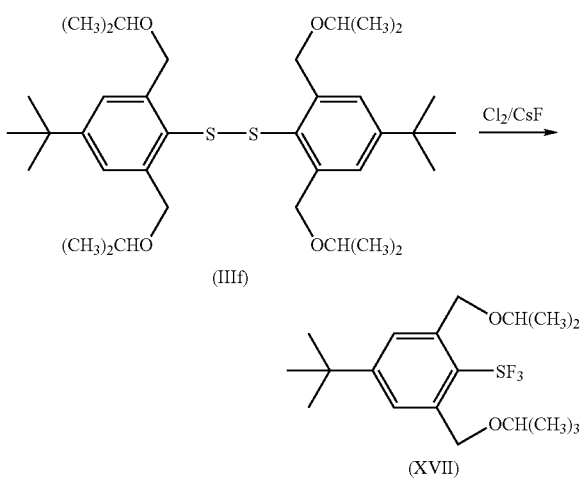

Using a synthesis procedure similar to the one described in Example 15d, 2,6-bis(isopropoxymethyl)-4-tert-butylphenylsulfur trifluoride (formula XVII, Table 3) was prepared. However, unlike Example 15d, bis[2,6-bis(isopropoxymethyl)-4-tert-butylphenyl]disulfide was used as a starting material. A yield of 61% was obtained. The physical and spectral data of the material are as follows: colorless liquid; bp 120° C./0.2 mmHg (bath temperature=145° C.); $^1$H NMR (CDCl$_3$) δ 1.24 (d, J=6 Hz, 12H, CH$_3$), 1.32 (s, 9H, C(CH$_3$)$_3$), 3.75 (septet, J=6.0 Hz, 2H, CH), 4.80 (br.s, 4H, CH$_2$), 7.55 (s, 2H, Ar—H); $^{19}$F NMR (CDCl$_3$) δ 48.73 (br.s, 2F, SF$_2$), −52.86 (br.s, 1F, SF); $^{13}$C NMR (CDCl$_3$) δ 21.99, 31.02, 35.05, 66.51, 71.93, 125.76, 139.50, 141.75, 154.62.

The present example illustrates the utility of the present invention for synthesizing fluorinating agents that can be used to produce fluorine-containing compounds.

Example 15f

Synthesis Embodiment of 2,6-bis(isobutoxymethyl)-4-tert-butylphenylsulfur trifluoride A Fluorinating Agent of the Present Invention

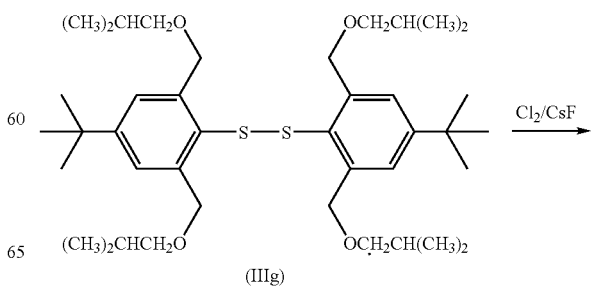

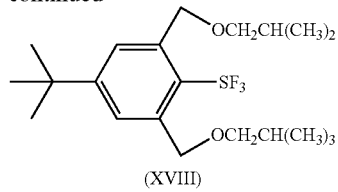

(XVIII)

Using a synthesis procedure similar to the one described in Example 15d, 2,6-bis(isobutoxymethyl)-4-tert-butylphenylsulfur trifluoride (formula XVIII, Table 3) was prepared. However, unlike Example 15d, bis[2,6-bis(isobutoxymethyl)-4-tert-butylphenyl]disulfide was used as a starting material. A yield of 60% was obtained. The physical and spectral data of the material are as follows: Colorless oil; bp 130° C./0.2 mmHg (bath temperature=150° C.); $^1$H NMR (CDCl$_3$) δ 0.97 (d, 12H, J=6 Hz, CH$_3$), 1.33 (s, 9H, C(CH$_3$)$_3$), 1.97 (m, 2H, CH), 3.33 (m, 4H, OCH$_2$), 4.89 (br.s, 4H, ArCH$_2$), 7.56 (broad peak, 2H, Ar—H); $^{19}$F NMR (CDCl$_3$) δ 47.42 (broad peak, 2F, SF$_2$), −53.15 (broad peak, 1F, SF); $^{13}$C-NMR (CDCl$_3$) δ 19.31, 28.62, 31.39, 35.08, 69.22, 77.90, 125.63, 139.14, 154.82, 156.94.

The present example illustrates the utility of the present invention for synthesizing fluorinating agents that can be used to produce fluorine-containing compounds.

Example 15g

Synthesis Embodiment of 2,6-bis(tert-butoxymethyl)-4-tert-butylphenylsulfur trifluoride A Fluorinating Agent of the Present Invention

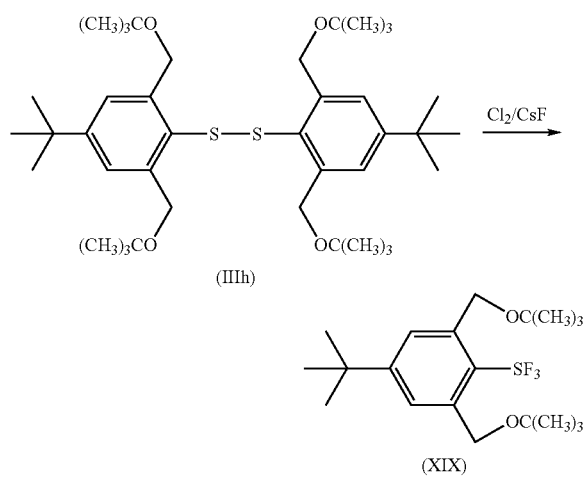

(IIIh)

(XIX)

A fluoropolymer flask was charged with 4.05 g (6.0 mmol) of bis[2,6-bis(tert-butoxymethyl)-4-tert-butylphenyl] disulfide, 18.2 g (120 mmol) of dry cesium fluoride and 35 mL of anhydrous acetonitrile. Chlorine gas (16.00 mmol, 1.70 g, 538 ml) was bubbled at the rate of 15 mL/min at 20° C. (water bath temperature). After passing chlorine, water bath was removed and mixture was stirred at room temperature for 1 hour. The solution was transferred by decantation under nitrogen atmosphere followed by washing with 15 mL of anhydrous acetonitrile. Acetonitrile was removed at room temperature to give a residue, which was extracted with anhydrous hexane. The hexane extract was evaporated to dryness, giving 3.3 g (70%) of 2,6-bis(tert-butoxymethyl)-4-tert-butylphenylsulfur trifluoride (formula XIX, Table 3) as a light yellow oil: $^1$H NMR (CDCl$_3$) δ 1.27 (s, 9H), 1.32 (s, 9H), 1.36 (s, 9H), 4.72 (s, 2H), 5.00 (s, 2H), 7.20 (s, 1H), 7.93 (s, 1H); $^{19}$F NMR (CDCl$_3$) δ 47.38 (br.s, 2F, SF$_2$), −53.20 (br.s, 1F, SF); $^{19}$F NMR (CDCl$_3$+THF (1:1)) δ 48.50 (2F, d, J=79 Hz, SF$_2$), −53.20 (1F, t, J=79 Hz, SF).

The present example illustrates the utility of the present invention for synthesizing fluorinating agents that can be used to produce fluorine-containing compounds.

Examples 16-25d

Thermal Analysis of Substituted Phenylsulfur Trifluorides

Thermal analysis was performed on compounds IV, IVa, IVb, V-XV of the present invention and PhSF$_3$ and p-CH$_3$C$_6$H$_4$SF$_3$ (Table 4). Decomposition temperature and exothermic heat (−ΔH) of each compound was determined using Differential Scanning Spectroscopy, i.e., using a Differential Scanning Spectrometer (DSC).

The decomposition temperature is the temperature at which onset of decomposition begins, and the exothermic heat is the amount of heat that results from the compounds decomposition. In general, a higher decomposition temperature and lower exothermic heat value provide compounds having greater thermal stability and provide greater safety.

Table 4 illustrates that the compounds of the present invention, the phenylsulfur trifluorides substituted with the alkyl group(s), a halogen atom(s), and/or the alkyl group(s) having ether linkage, show unexpected and significant improvement in decomposition temperature and exothermic heat values over the useful conventional fluorinating agents (DAST and Deoxo-Fluor®). This data illustrates the improved thermal stability of the compounds of the invention and, as a result, the improved safety of the compounds of the invention over other useful conventional fluorinating agents. Phenylsulfur trifluoride (PhSF$_3$) and p-methylphenylsulfur trifluoride (p-CH$_3$C$_6$H$_4$SF$_3$) have high decomposition temperatures, but they have high exothermic heat and their fluorination reactivity is low (see Examples below).

TABLE 4

Thermal Analysis Data of Substituted Phenylsulfur Trifluorides (Formulas IV~XV) and Prior Art PhSF$_3$, p-CH$_3$C$_6$H$_4$SF$_3$, DAST and Deoxo-Fluor ®

| | Compound | Decomposition temp.(° C.) | −ΔH(J/g) |
|---|---|---|---|
| Ex. 16 | IV; $R^{1a} = R^{1b} = CH_3$, $R^{2a} = R^{2b} = H$, $R^3 = C(CH_3)_3$ | 232 | 544 |
| Ex. 16a | IVa; $R^{1a} = R^{1b} = CH_3$, $R^{2a} = Cl$, $R^{2b} = H$, $R^3 = C(CH_3)_3$ | 227 | 520 |
| Ex. 16b | IVb; $R^{1a} = R^{1b} = CH_3$, $R^{2a} = R^{2b} = Cl$, $R^3 = C(CH_3)_3$ | 238 | 392 |
| Ex. 17 | V; $R^{1a} = R^{1b} = R^{2a} = R^{2b} = H$, $R^3 = C(CH_3)_3$ | 319 | 700 |

TABLE 4-continued

Thermal Analysis Data of Substituted Phenylsulfur Trifluorides (Formulas IV~XV) and Prior Art PhSF$_3$, p-CH$_3$C$_6$H$_4$SF$_3$, DAST and Deoxo-Fluor ®

| | Compound | Decomposition temp.(° C.) | −ΔH(J/g) |
|---|---|---|---|
| Ex. 18 | VI; R$^{1a}$ = R$^{1b}$ = CH$_3$, R$^{2a}$ = R$^{2b}$ = H, R$^3$ = CH$_3$ | 209 | 462 |
| Ex. 19 | VII; R$^{1a}$ = CH$_3$ R$^{1b}$ = H, R$^{2a}$ = R$^{2b}$ = H, R$^3$ = CH$_3$ | 222 | 625 |
| Ex. 20 | VIII; R$^{1a}$ = CH$_3$, R$^{1b}$ = H, R$^{2a}$ = H, R$^{2b}$ = CH$_3$, R$^3$ = H | 228 | 486 |
| Ex. 21 | IX; R$^{1a}$ = R$^{1b}$ = CH$_3$, R$^{2a}$ = R$^{2b}$ = R$^3$ = H | 225 | 595 |
| Ex. 22 | X; R$^{1a}$ = R$^{1b}$ = R$^{2a}$ = R$^{2b}$ = H, R$^3$ = F | 297 | 368 |
| Ex. 23 | XI; R$^{1a}$ = R$^{1b}$ = R$^{2a}$ = R$^{2b}$ = H, R$^3$ = Cl | 311 | 458 |
| Ex. 24 | XII; R$^{1a}$ = R$^{1b}$ = H, R$^{2a}$ = CH$_3$, R$^{2b}$ = H, R$^3$ = Cl | 299 | 391 |
| Ex. 25 | XIII; R$^{1a}$ = R$^{1b}$ = CH(CH$_3$)$_2$, R$^{2a}$ = R$^{2b}$ = H, R$^3$ = CH(CH$_3$)$_2$ | 215 | 552 |
| Ex. 25a | XIV; R$^{1a}$ = R$^{1b}$ = CH$_2$OCH$_3$, R$^{2a}$ = R$^{2b}$ = H, R$^3$ = H | 175 | 585 |
| Ex. 25b | XV; R$^{1a}$ = R$^{1b}$ = CH$_2$OCH$_3$, R$^{2a}$ = R$^{2b}$ = H, R$^3$ = C(CH$_3$)$_3$ | 192 | 674 |
| Ex. 25c | PhSF$_3$ | 305 | 826 |
| Ex. 25d | p-CH$_3$C$_6$H$_4$SF$_3$ | 274 | 1096 |
| | (C$_2$H$_5$)$_2$N—SF$_3$ (DAST) | ~140 | 1700 |
| | (CH$_3$OCH$_2$CH$_2$)$_2$N—SF$_3$ (Deoxo-Fluor ®) | ~140 | 1100 |

Examples 26-55

Fluorination of Target Compounds Using the Compounds of the Present Invention

Many procedures are provided for fluorinating a target compound using the fluorinating agents of the present invention. Ten procedures are described as procedures A-J:

Procedure A: In a 10 mL fluoropolymer (PFA)-bottle (equipped with an N$_2$ inlet tube, septum and magnetic stir bar): 65 mg of benzyl alcohol (0.604 mmol) was added to a solution of 166 mg 2,6-dimethyl-4-tert-butylphenylsulfur trifluoride (formula IV) (0.664 mmol) in 3 mL anhydrous CH$_2$Cl$_2$. The addition was performed at room temperature under a stream of N$_2$. The mixture was allowed to stir at room temperature. The progress of the reaction was monitored by gas chromatography (GC). After 2 hours a $^{19}$F-NMR analysis was performed indicating that benzyl fluoride was obtained (88% yield).

Procedure B: In a 5 mL fluoropolymer-bottle (equipped with an N$_2$ inlet tube, septum and magnetic stir bar): 42 mg isovaleraldehyde (0.491 mmol) was added to a solution of 135 mg 2,6-dimethyl-4-tert-butylphenylsulfur trifluoride (formula IV) (0.540 mmol) in 0.5 mL anhydrous CH$_2$Cl$_2$. The addition was performed at room temperature under a stream of N$_2$. The mixture was allowed to stir at room temperature. The progress of the reaction was monitored by GC. After 24 hours a $^{19}$F-NMR analysis was performed indicating that 1,1-difluoro-3-methylbutane was obtained (95% yield).

Procedure C: In a 5 mL fluoropolymer-bottle (equipped with an N$_2$ inlet tube, septum and magnetic stir bar): 40 mg cyclohexanone (0.405 mmol) was added to a solution of 172 mg 2,6-dimethyl-4-tert-butylphenylsulfur trifluoride (formula IV) (0.688 mmol) in 0.5 mL anhydrous CH$_2$Cl$_2$. The addition was performed at room temperature under a stream of N$_2$. Ethanol (3.7 mg, 0.08 mmol) was added to the reaction and the reaction allowed to stir at room temperature. The progress of the reaction was monitored by GC. After 24 hours a $^{19}$F-NMR analysis was performed indicating that 1,1-difluorocyclohexane was obtained (74% yield).

The purpose of the addition of ethanol in Procedure C is to make hydrogen fluoride (HF), which accelerates the fluorination reaction as a catalyst. Ethanol reacts with the SF$_3$ fluorinating agent to HF together with ethyl fluoride.

Procedure D: In a 1 mL fluoropolymer tube: 21 mg benzoic acid (0.170 mmol) was added to 106 mg 2,6-dimethyl-4-tert-butylphenylsulfur trifluoride (formula IV) (0.424 mmol). The addition was made at room temperature under a stream of N$_2$. The tube was then sealed and heated at 100° C. The progress of the reaction was monitored by GC. After 2 hours a $^{19}$F-NMR analysis was performed indicating that α,α,α-trifluorotoluene was obtained (88% yield).

Procedure E: A 5 mL fluoropolymer vessel was charged with 1.0 g (4.55 mmol) of p-heptylbenzoic acid and 3.4 g (13.65 mmol) of a 93:7 (mol ratio) mixture of 2,6-dimethyl-4-tert-butylphenylsulfur trifluoride (formula IV) and 2,4-dimethyl-3-chloro-4-tert-butylphenylsulfur trifluoride (formula IVa), in a dry box. The reaction vessel was then brought out from the dry box. 1.0 mL of hydrogen fluoride pyridine (a mixture of ~70% of HF and ~30% of pyridine) was slowly added into the reaction mixture under nitrogen. The reaction mixture was slowly heated to 50° C., and kept at that temperature for 22 hours. The NMR analysis showed that p-heptylbenzotrifluoride was produced in 74% yield.

Procedure F: In a dry box, 0.500 g (2.72 mmol) of O-phenyl S-methyl dithiocarbonate and 3.4 g (13.6 mmol) of a 93:7 (mol ratio) mixture of 2,6-dimethyl-4-tert-butylphenylsulfur trifluoride (formula IV) and 2,4-dimethyl-3-chloro-4-tert-butylphenylsulfur trifluoride (formula IVa) were put in a 5 mL fluoropolymer vessel. The mixture was slowly heated to 80° C. and maintained at the temperature for 19 hours. The NMR analysis using a sample showed that phenyl trifluoromethyl ether was produced in 92% yield. $^{19}$F NMR for PhOCF$_3$ (CDCl$_3$): −58.22 (s, 3F, CF$_3$).

Procedure G: In a dry box, 0.912 g (6 mmol) of O-methyl thiobenzoate and 1.8 g (7.2 mmol) of a 93:7 (mol ratio) mixture of 2,6-dimethyl-4-tert-butylphenylsulfur trifluoride (formula IV) and 2,4-dimethyl-3-chloro-4-tert-butylphenylsulfur trifluoride (formula IVa) were put in a 5 mL fluoropolymer vessel. Then, the reaction mixture was heated to 100° C. under N$_2$ for 2 hours. The reaction mixture changed from initial light green to pink. The NMR analysis showed that methyl phenyldifluoromethyl ether was produced in 95% yield. $^{19}$F NMR for PhCF$_2$OCH$_3$ (CDCl$_3$) δ −72.17 (s, 2F, CF$_2$).

Procedure H: In a dry box, 0.304 mg (2 mmol) of O-methyl thiobenzoate was dissolved in 2 mL of dry CH$_2$Cl$_2$ in a 5 mL fluoropolymer vessel. Then, 0.6 g (2.4 mmol) of a 93:7 (mol ratio) mixture of 2,6-dimethyl-4-tert-butylphenylsulfur trifluoride (formula IV) and 2,4-dimethyl-3-chloro-4-tert-butylphenylsulfur trifluoride (formula IVa) was added to the solution, and 15 mg (0.066 mmol) of $SbCl_3$ was added to the reaction mixture. The reaction mixture was stirred under $N_2$ at room temperature for 26 hours. The NMR analysis showed that methyl phenyldifluoromethyl ether was produced in 78% yield.

Procedure I: In a dry box, 0.31 g (1.58 mmol) of 2-phenyl-1,3-dithiane was dissolved in 2 mL anhydrous $CH_2Cl_2$ in a 5 mL fluoropolymer vessel. Then 1.0 g (4.0 mmol) of a 93:7 (mol ratio) mixture of 2,6-dimethyl-4-tert-butylphenylsulfur trifluoride (formula IV) and 2,4-dimethyl-3-chloro-4-tert-butylphenylsulfur trifluoride (formula IVa) was added to the reaction mixture. Slight exothermic reaction occurred. The reaction mixture was then stirred at room temperature for 2 hours under $N_2$. The NMR analysis showed that difluoromethylbenzene was produced in 82% yield. $^{19}F$ NMR for $PhCF_2H(CDCl_3)$ δ −110.54 (d, J=60.7 Hz, $CF_2$).

Procedure J: In a 15 mL fluoropolymer flask, 2,6-dimethyl-4-tert-butylphenylsulfur trifluoride (0.625 g, 2.5 mmol) was dissolved in 5 mL of anhydrous $CH_2Cl_2$. A solution of meso-1,2-diphenyl-1,2-ethanediol (0.214 g, 1.0 mmol) in 5 mL of anhydrous $CH_2Cl_2$ was added to the above stirred solution at room temperature. After 3 hours, $C_{12}H_{26}F$ was added as standard, the $^{19}F$ NMR analysis showed that 1,2-difluoro-1,2-diphenylethane ($PhCHFCHFPh$) was produced in 97% yield and a trace (~0.03%) of 1,1-difluoro-2,2-diphenylethane ($Ph_2CHCF_2H$) was formed. Products were characterized by comparing to the spectroscopic data in literature (see Journal of Fluorine Chem. Vol. 125, pp 1869-1872 (2004)).

Referring to Table 5: Examples 26-28, 28a, 29-32,32a-f, 33-44, 44a, 54, 55 and reactions with a known fluorinating agent ($PhSF_3$) (Comparison Example 1) and a known and similar compound ($p-CH_3C_6H_4SF_3$) [J. Am. Chem. Soc., Vol. 84, pp 3058-3063 (1962)] (Comparison Example 2) were carried out under the reaction conditions shown in Table 5 and according to procedure A; Examples 45,45a-c, 48, 48a,b, 49, 49a,b, and 50 were carried out under the reaction conditions shown in Table 5 and according to procedure B; Examples 46, 46a,b, 47 and 47a,b were carried out under the conditions shown in Table 5 and according to procedure C; and Examples 51, 51a, 52, 52a, 53, and 53a were carried out under the conditions shown in Table 5 and according to procedure D. The procedures E, F, G, H and I are for Examples 49c, 55a, 55b, 55c and 55d, respectively. The Procedure J is for Examples 55e and 55f and Comparison Examples 3 and 4.

TABLE 5

Fluorinations of Various Organic Target Compounds with Substituted Phenylsulfur Trifluorides (Formulas IV, IVa,b, V~XVIII), Prior Art Compounds ($PhSF_3$ and $p-CH_3C_6H_4SF_3$), and Conventional Fluorinating Agents (DAST and Deoxo-Fluor ®).

| | Phenyl-sulfur trifluorides | Organic compounds | Reaction conditions Solv, Temp | Additive | Time | Fluorinated compounds Chemical structure | Yield |
|---|---|---|---|---|---|---|---|
| Comp. Ex. 1 | $PhSF_3$ | $PhCH_2OH$ | $CH_2Cl_2$ r.t. | | 2 h | $PhCH_2F$ | 25% |
| Comp. Ex. 2 | $p-CH_3C_6H_4SF_3$ | $PhCH_2OH$ | $CH_2Cl_2$ r.t. | | 2 h | $PhCH_2F$ | 19% |
| Ex. 26 | IV | $PhCH_2OH$ | $CH_2Cl_2$ r.t. | | 2 h | $PhCH_2F$ | 88% |
| Ex. 27 | V | $PhCH_2OH$ | $CH_2Cl_2$ r.t. | | 2 h | $PhCH_2F$ | 52% |
| Ex. 28 | VI | $PhCH_2OH$ | $CH_2Cl_2$ r.t. | | 2 h | $PhCH_2F$ | 38% |
| Ex. 28a | VII | $PhCH_2OH$ | $CH_2Cl_2$ r.t. | | 2 h | $PhCH_2F$ | 55% |
| Ex. 29 | VIII | $PhCH_2OH$ | $CH_2Cl_2$ r.t. | | 2 h | $PhCH_2F$ | 46% |
| Ex. 30 | IX | $PhCH_2OH$ | $CH_2Cl_2$ r.t. | | 2 h | $PhCH_2F$ | 40% |
| Ex. 31 | XI | $PhCH_2OH$ | $CH_2Cl_2$ r.t. | | 2 h | $PhCH_2F$ | 37% |
| Ex. 32 | XIII | $PhCH_2OH$ | $CH_2Cl_2$ r.t. | | 2 h | $PhCH_2F$ | 46% |
| Ex. 32a | IVb | $PhCH_2OH$ | $CH_2Cl_2$ r.t. | | 2 h | $PhCH_2F$ | 90% |
| Ex. 32b | XIV | $PhCH_2OH$ | $CH_2Cl_2$ r.t. | | 2 h | $PhCH_2F$ | 95% |
| Ex. 32c | XV | $PhCH_2OH$ | $CH_2Cl_2$ r.t. | | 2 h | $PhCH_2F$ | 90% |
| Ex. 32d | XVI | $PhCH_2OH$ | $CH_2Cl_2$ r.t. | | 2 h | $PhCH_2F$ | 78% |
| Ex. 32e | XVII | $PhCH_2OH$ | $CH_2Cl_2$ r.t. | | 2 h | $PhCH_2F$ | 83% |
| Ex. 32f | XVIII | $PhCH_2OH$ | $CH_2Cl_2$ r.t. | | 2 h | $PhCH_2F$ | 93% |
| Ex. 33 | IV | $n-C_{12}H_{25}OH$ | $CH_2Cl_2$ r.t. | | 6 h | $n-C_{12}H_{25}F$ | 91% |
| Ex. 34 | V | $n-C_{12}H_{25}OH$ | $CH_2Cl_2$ r.t. | | 6 h | $n-C_{12}H_{25}F$ | 77% |
| Ex. 35 | VI | $n-C_{12}H_{25}OH$ | $CH_2Cl_2$ r.t. | | 6 h | $n-C_{12}H_{25}F$ | 61% |
| Ex. 36 | VII | $n-C_{12}H_{25}OH$ | $CH_2Cl_2$ r.t. | | 6 h | $n-C_{12}H_{25}F$ | 68% |
| Ex. 37 | X | $n-C_{12}H_{25}OH$ | $CH_2Cl_2$ r.t. | | 6 h | $n-C_{12}H_{25}F$ | 66% |
| Ex. 38 | XI | $n-C_{12}H_{25}OH$ | $CH_2Cl_2$ r.t. | | 6 h | $n-C_{12}H_{25}F$ | 66% |
| Ex. 39 | IV | $n-C_{10}H_{21}CH(OH)CH_3$ | $CH_2Cl_2$ r.t. | | 6 h | $n-C_{10}H_{21}CHFCH_3$ | 75% |
| Ex. 40 | V | $n-C_{10}H_{21}CH(OH)CH_3$ | $CH_2Cl_2$ r.t. | | 6 h | $n-C_{10}H_{21}CHFCH_3$ | 72% |
| Ex. 41 | VI | $n-C_{10}H_{21}CH(OH)CH_3$ | $CH_2Cl_2$ r.t. | | 6 h | $n-C_{10}H_{21}CHFCH_3$ | 70% |
| Ex. 42 | VII | $n-C_{10}H_{21}CH(OH)CH_3$ | $CH_2Cl_2$ r.t. | | 6 h | $n-C_{10}H_{21}CHFCH_3$ | 54% |
| Ex. 43 | X | $n-C_{10}H_{21}CH(OH)CH_3$ | $CH_2Cl_2$ r.t. | | 6 h | $n-C_{10}H_{21}CHFCH_3$ | 49% |
| Ex. 44 | XI | $n-C_{10}H_{21}CH(OH)CH_3$ | $CH_2Cl_2$ r.t. | | 6 h | $n-C_{10}H_{21}CHFCH_3$ | 47% |
| Ex. 44a | XV | $n-C_{10}H_{21}CH(OH)CH_3$ | $CH_2Cl_2$ r.t. | | 6 h | $n-C_{10}H_{21}CHFCH_3$ | 77% |
| Ex. 45 | IV | $(CH_3)_2CHCH_2CHO$ | $CH_2Cl_2$ r.t. | | 1 day | $(CH_3)_2CHCH_2CF_2H$ | 95% |
| Ex. 45a | XIV | PhCHO | $CH_2Cl_2$ r.t. | | 4 h | $PhCF_2H$ | 84% |
| Ex. 45b | XV | PhCHO | $CH_2Cl_2$ r.t. | | 4 h | $PhCF_2H$ | 96% |
| Ex. 45c | XVII | PhCHO | $CH_2Cl_2$ r.t. | | 2 h | $PhCF_2H$ | 80% |
| Ex. 46 | IV | Cyclohexanone | $CH_2Cl_2$ r.t. | EtOH(HF) | 1 day | 1,1-diF-cyclohexane | 74% |
| Ex. 46a | XIV | Cyclohexanone | $CH_2Cl_2$ r.t. | EtOH(HF) | 6 h | 1,1-diF-cyclohexane | 70% |
| Ex. 46b | XV | Cyclohexanone | $CH_2Cl_2$ r.t. | EtOH(HF) | 6 h | 1,1-diF-cyclohexane | 72% |

TABLE 5-continued

Fluorinations of Various Organic Target Compounds with Substituted Phenylsulfur Trifluorides (Formulas IV, IVa,b, V~XVIII), Prior Art Compounds (PhSF$_3$ and p-CH$_3$C$_6$H$_4$SF$_3$), and Conventional Fluorinating Agents (DAST and Deoxo-Fluor ®).

| | Phenyl-sulfur trifluorides | Organic compounds | Reaction conditions Solv, Temp | Additive | Time | Fluorinated compounds Chemical structure | Yield |
|---|---|---|---|---|---|---|---|
| Ex. 47 | IV | n-C$_{11}$H$_{23}$COCH$_3$ | CH$_2$Cl$_2$ r.t. | EtOH(HF) | 1 day | n-C$_{11}$H$_{23}$CF$_2$CH$_3$ | 100% |
| Ex. 47a | XIV | n-C$_{11}$H$_{23}$COCH$_3$ | CH$_2$Cl$_2$ r.t. | EtOH(HF) | 1 day | n-C$_{11}$H$_{23}$CF$_2$CH$_3$ | 100% |
| Ex. 47b | XV | n-C$_{11}$H$_{23}$COCH$_3$ | CH$_2$Cl$_2$ r.t. | EtOH(HF) | 1 day | n-C$_{11}$H$_{23}$CF$_2$CH$_3$ | 100% |
| Ex. 48 | IV | PhCOOH | CH$_2$Cl$_2$ r.t. | | 2 day | PhCOF | 100% |
| Ex. 48a | XIV | PhCOOH | CH$_2$Cl$_2$ r.t. | | 1 day | PhCOF | 100% |
| Ex. 48b | XV | PhCOOH | CH$_2$Cl$_2$ r.t. | | 1 day | PhCOF | 100% |
| Ex. 49 | IV | n-C$_{11}$H$_{23}$COOH | CH$_2$Cl$_2$ r.t. | | 1 day | n-C$_{11}$H$_{23}$COF | 97% |
| Ex. 49a | XIV | n-C$_{11}$H$_{23}$COOH | CH$_2$Cl$_2$ r.t. | | 1 day | n-C$_{11}$H$_{23}$COF | 100% |
| Ex. 49b | XV | n-C$_{11}$H$_{23}$COOH | CH$_2$Cl$_2$ r.t. | | 1 day | n-C$_{11}$H$_{23}$COF | 100% |
| Ex. 49c | IV(93%) + IVa(7%) | p-(n-C$_7$H$_{15}$)C$_6$H$_4$COOH | HF/py 50° C. | HF/py | 22 h | p-(n-C$_7$H$_{15}$)C$_6$H$_4$CF$_3$ | 74% |
| Ex. 50 | IV | PhCOCl | CH$_2$Cl$_2$ r.t. | | 2 day | PhCOF | 51% |
| Ex. 51 | IV | PhCOOH | Non 100° C. | | 2 h | PhCF$_3$ | 89% |
| Ex. 51a | XIV | PhCOOH | Non 100° C. | | 2 h | PhCF$_3$ | 50% |
| Ex. 52 | IV | p-(n-C$_7$H$_{15}$)C$_6$H$_4$COOH | Non 100° C. | | 2 h | p-(n-C$_7$H$_{15}$)C$_6$H$_4$CF$_3$ | 88% |
| Ex. 52a | XIV | p-(n-C$_7$H$_{15}$)C$_6$H$_4$COOH | Non 100° C. | | 2 h | p-(n-C$_7$H$_{15}$)C$_6$H$_4$CF$_3$ | 53% |
| Ex. 53 | IV | n-C$_{11}$H$_{23}$COOH | Non 100° C. | | 2 h | n-C$_{11}$H$_{23}$CF$_3$ | 55% |
| Ex. 53a | XIV | n-C$_{11}$H$_{23}$COOH | Non 100° C. | | 2 h | n-C$_{11}$H$_{23}$CF$_3$ | 60% |
| Ex. 54 | IV | PhSCH$_3$ | CH$_2$Cl$_2$ r.t. | | 20 min | PhSCH$_2$F | 61% |
| Ex. 55 | IV | PhSOC$_3$ | CH$_2$Cl$_2$ r.t. | | 24 h | PhSCH$_2$F | 41% |
| Ex. 55a | IV(93%) + IVa(7%) | PhOC(=S)SCH$_3$ | Non 60° C. | | 15 h | PhOCF$_2$OCH$_3$ | 86% |
| Ex. 55b | IV(93%) + IVa(7%) | PhC(=S)OCH$_3$ | Non 100° C. | | 2 h | PhCF$_2$OCH$_3$ | 95% |
| Ex. 55c | IV(93%) + IVa(7%) | PhC(=S)OCH$_3$ | CH$_2$Cl$_2$ r.t. | SbCl$_3$ | 26 h | PhCF$_2$OCH$_3$ | 78% |
| Ex. 55d | IV(93%) + IVa(7%) | 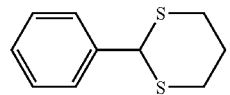 | CH$_2$Cl$_2$ r.t. | | 2 h | PhCF$_2$H | 82% |
| Ex. 55e | IV | PhCH(OH)CH(OH)Ph | CH$_2$Cl$_2$ r.t. | | 3 h | PhCHFCHFPh / Ph$_2$CHCF$_2$H | 97% / ~0.03% |
| Ex. 55f | XV | PhCH(OH)CH(OH)Ph | CH$_2$Cl$_2$ r.t. | | 24 h | PhCHFCHFPh / Ph$_2$CHCF$_2$H | 98.5% / ~0.04% |
| Comp. Ex. 3 | DAST | PhCH(OH)CH(OH)Ph | CH$_2$Cl$_2$ r.t. | | 3 h | PhCHFCHFPh / Ph$_2$CHCF$_2$H | 51% / 13% |
| Comp. Ex. 4 | Deoxo-Fluor ® | PhCH(OH)CH(OH)Ph | CH$_2$Cl$_2$ r.t. | | 3 h | PhCHFCHFPh / Ph$_2$CHCF$_2$H | 36% / 18% |

PhSF$_3$ = phenylsulfur trifluoride;
p-CH$_3$C$_6$H$_4$SF$_3$ = p-methylphenylsulfur trifluoride;
r. t. = room temperature;
Non = No solvent;
p-(n-C$_7$H$_{15}$)C$_6$H$_4$COOH = p-(n-heptyl)benzoic acid;
PhSCH$_3$ = thioanisole;
PhSOCH$_3$ = methyl phenyl sulfoxide;
EtOH = ethanol;
py = pyridine;
PhOC(=S)SCH$_3$ = O-phenyl S-methyl dithiocarbonate;
PhC(=S)OCH$_3$ = O-methyl thiobenzoate.

As shown from the data in Table 5, it has been unexpectedly shown that the novel substituted phenylsulfur trifluorides of the invention, the phenylsulfur trifluorides substituted with the alkyl group(s), the halogen atom(s), and/or the alkyl group(s) having ether linkage, are much more effective fluorinating agents than the known and similar PhSF$_3$ (Comparison Example 1) and p-CH$_3$C$_6$H$_4$SF$_3$ (Comparison Example 2). Furthermore, as seen from the comparison between Examples 55e and 55f and Comparison Examples 3 and 4, the novel substituted phenylsulfur trifluorides of the invention have high yields and high selectivity in fluorination compared to conventional fluorinating agents such as DAST and Deoxo-Fluor®. In addition, the present examples illustrate that the novel compounds of the invention can fluorinate a wide variety of target compounds with high yields. Example 54 shows the utility of the present invention where a hydrogen atom located at the germinal position of the sulfur atom is replaced with fluorine. In addition, Example 55 also illustrates replacement of a hydrogen atom with fluorine.

Examples 56~63 and Comparison Examples 5~8

Stability, Safety, and Disposability of the Substituted Phenylsulfur Trifluorides and the Conventional Sulfur Trifluorides Stability, safety, and disposability of the substituted phenylsulfur trifluorides, IV, IVa,b, XIV~XVIII, and conventional sulfur trifluorides, such as DAST, Deoxo-Fluor®, phenylsulfur trifluoride (PhSF$_3$), and p-methylphenylsulfur trifluoride (p-CH$_3$C$_6$H$_4$SF$_3$) were examined by testing for hydrolytic stability. The visual hydrolytic stability test was conducted by adding approximately 10-50 mg of sulfur trifluoride ("dropwise") onto a large excess of water in a beaker at room temperature. Each compound tested was evaluated according to a 1~10 evaluation, where:

A. reaction when dropped—
10=Instant vigorous reaction occurs;
5=Instant mild reaction occurs; and
1=No instant reaction occurs.

B. sound emission when dropped—
10=Instant very loud sound occurs;
5=Instant mild sound occurs; and
1=No sound occurs.

C. fume production when dropped—
10=Instant much fume produced;
5=Instant mild fume produced; and
1=No fume produced.

The results are summarized in Table 6. The term "No instant reaction occurs" means that there was observed no apparent change of the sulfur trifluoride when the tested material was dropped onto the water.

TABLE 6

Visible Stability in Water of Substituted Phenylsulfur Trifluorides (Formulas IV, IVa, b, and XIV-XVIII), Prior Art Compounds (PhSF$_3$ and p-CH$_3$C$_6$H$_4$SF$_3$), and Useful Conventional Fluorinating Agents (DAST and Deoxo-Fluor ®)

| Ex. | Sulfur trifluoride | Reaction when dropped | Sound when dropped | Fume when dropped |
|---|---|---|---|---|
| Comparison Ex. 5 | DAST | 10 | 10 | 10 |
| Comparison Ex. 6 | Deoxy-Fluor ® | 10 | 10 | 10 |
| Comparison Ex. 7 | PhSF$_3$ | 5 | 5 | 5 |
| Comparison Ex. 8 | p-CH$_3$C$_6$H$_4$SF$_3$ | 5 | 5 | 5 |
| Ex. 56 | IV | 1 (No evident reaction after 10 min.) | 1 | 1 |
| Ex. 57 | IV(93 mol %) + IVa(7 mol %) | 1 (No evident reaction after 10 min) | 1 | 1 |
| Ex. 58 | IVb | 1 (Reaction started after ca. 20 sec)*$^1$ | 1 | 1 |
| Ex. 59 | XIV | 1 (Reaction started after ca. 45 sec)*$^2$ | 1 | 1 |
| Ex. 60 | XV | 1 (Reaction started after ca. 5 min)*$^3$ | 1 | 1 |
| Ex. 61 | XVI | 1*$^4$ | 1 | 1 |
| Ex. 62 | XVII | 1*$^5$ | 1 | 1 |
| Ex. 63 | XVIII | 1*$^6$ | 1 | 1 |

*$^1$After ca. 20 sec, the surface of the drop started to change milky indicating hydrolysis.
*$^2$After ca. 45 sec, the surface of the drop started to change milky indicating hydrolysis.
*$^3$After ca. 5 min, the surface of the drop started to change milky indicating hydrolysis.
*$^4$After ca. 20 sec, the surface of the drop partially started to changed to change milky indicating hydrolysis, but the hydrolysis was very slow.
*$^5$After several seconds, the surface of the drop partially started to change milky indicating hydrolysis, but the hydrolysis was very slow.
*$^6$After ca. 5 sec, the surface of the drop partially started to change milky indicating hydrolysis, but the hydrolysis was very slow.

Conventional fluorinating agents such as DAST and Deoxo-Fluor® are known to be extremely sensitive to moisture and easily hydrolyzed and therefore dangerous when contacted with water (extremely vigorous reaction with water as seen from Table 6). Phenylsulfur trifluoride and p-methylphenylsulfur trifluoride are similar to DAST and Deoxo-Fluor® in this manner. Contrary to this, substituted phenylsulfur trifluorides of the present invention, the phenylsulfur trifluorides substituted with the alkyl group(s), the halogen atom(s), and/or the alkyl groups having ether linkage, such as IV, IVa,b, and XIV-XVIII, have a relatively high stability to water. This indicates that the substituted phenylsulfur trifluorides have high stability, storage stability, safety, safe handling, and safe disposability. From the comparison between Examples 56~58 and Comparison Examples 7 and 8, the alkyl group and the halogen substituents of the present invention unexpectedly and surprisingly improve the compounds of the invention's stability to hydrolysis. From the comparison between Example 59 and Comparison Example 7, the alkyl groups having one or more ether linkages have high stability. This also demonstrates that the alkyl group, having at least one ether linkage, unexpectedly and surprisingly improves the stability of the phenylsulfur trifluorides of the invention.

Example 64

Methanolysis experiment of a 93:7 (mol ratio) mixture of 2,6-dimethyl-4-tert-butylphenylsulfur trifluoride (IV) and 2,6-dimethyl-3-chloro-4-tert-butylphenylsulfur trifluoride (IVa)

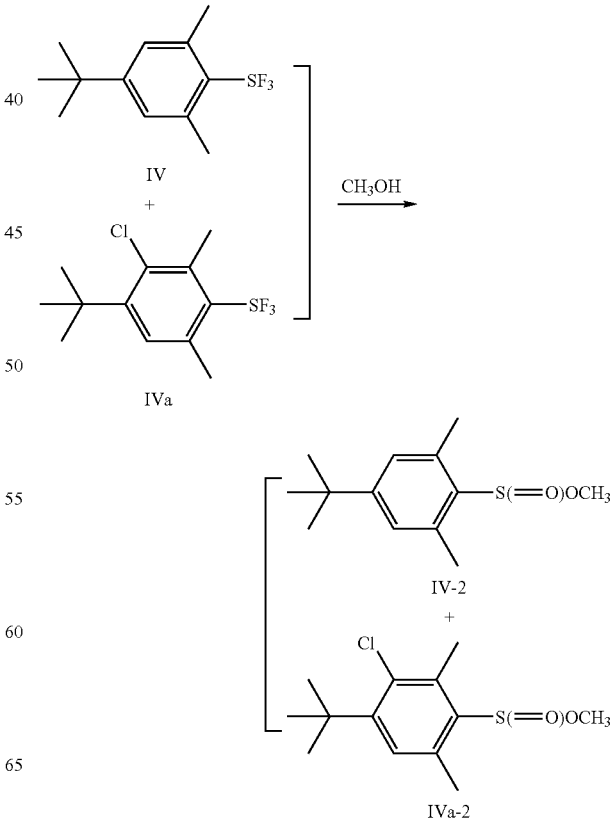

A fluoropolymer vessel was charged with 5 g of a 93:7 (mol ratio) mixture of 2,4-dimethyl-4-tert-butylphenylsulfur trifluoride (IV) and 2,4-dimethyl-3-chloro-4-tert-butylphenylsulfur trifluoride (IVa) in dry box. 10 mL of anhydrous CH$_3$OH was slowly added to this mixture. Exothermic reaction occurred during the addition. After addition, the reaction mixture was stirred under N$_2$ for 30 min. The reaction mixture was poured into 20 mL of cold aqueous Na$_2$CO$_3$ solution and then extracted with ether. The organic layer was separated and dried over anhydrous MgSO$_4$, and evaporated to give a light yellow product. Recrystallization from cold hexanes yielded a white solid (4.2 g). $^1$H-NMR analysis of the solid indicated that the solid is a mixture of 92% of compound IV-2 and 8% of compound IVa-2.

Compound IV-2: $^1$H-NMR (CDCl$_3$) δ 7.04 (s, 2H, Ar—H), 3.80 (s, 3H, S(O)OCH$_3$), 2.62 (s, 6H, Ar—CH$_3$), 1.28 (s, 9H, C(CH$_3$)$_3$); GC-Mass 240 (M$^+$).

Compound IVa-2: $^1$H-NMR (CDCl$_3$) δ 7.12 (s, 1H, Ar—H), 3.83 (s, 3H, S(O)OCH$_3$), 2.66 (s, 6H, Ar—CH$_3$), 1.47 (s, 9H, C(CH$_3$)$_3$); GC-Mass 276 (M$^+$), 274 (M$^+$).

The formation of these products can be explained by the following mechanism as shown in the scheme below. The methanolysis consists of two steps, a first methanolysis followed by a second methanolysis. The first methanolysis of compounds, formula IV and IVa, give sulfinyl fluorides, IV-1 and IVa-1, methyl fluoride (CH$_3$F) and hydrogen fluoride (HF), and the second methanolysis leads to the final products, IV-2 and IVa-2.

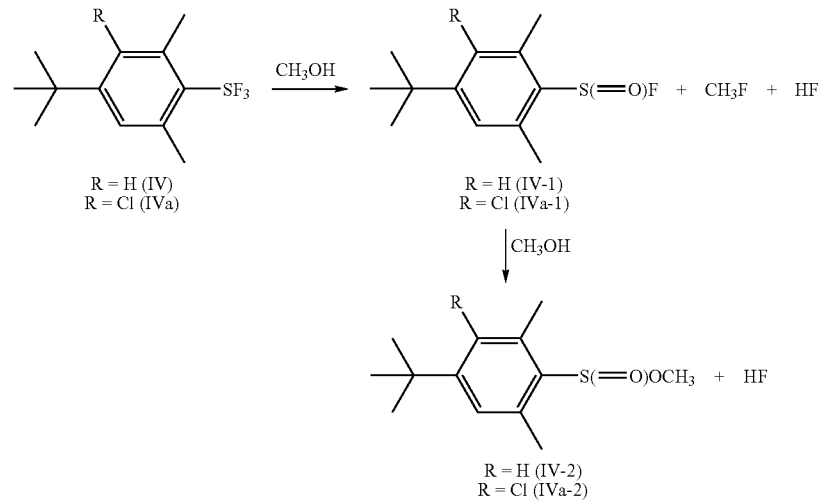

The first methanolysis reaction corresponds to the fluorination reaction of target compounds containing oxygen atoms. This indicates that the fluorination reactions of the target compounds provide sulfinyl fluorides such as IV-1 and IVa-1 in addition to the fluorinated products. When the sulfinyl fluorides are further hydrolyzed with water, aqueous acidic solution or basic solution, the corresponding sulfinic acids or their salts are formed.

It is understood for purposes of this disclosure, that various changes and modifications may be made to the invention that are well within the scope of the invention. Numerous other changes may be made which will readily suggest themselves to those skilled in the art which are encompassed in the spirit of the invention disclosed herein and as defined in the appended claims.

This specification contains numerous citations to references such as patents, patent applications, and publications. Each is hereby incorporated by reference for all purposes.

What is claimed is:

1. A compound of the formula (I):

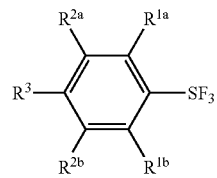

in which

R$^{1a}$ and R$^{1b}$ are independently a hydrogen atom; a primary or secondary alkyl group having from one to eight carbon atoms; or a primary, secondary, or tertiary alkyl group having two to eight carbon atoms and at least one ether linkage; and R$^{2a}$, R$^{2b}$, and R$^3$ are independently a hydrogen atom; a halogen atom; a primary, secondary, or tertiary alkyl group having from one to eight carbon atoms; or a primary, secondary, or tertiary alkyl group having two to eight carbon atoms and at least one ether linkage; and wherein, when R$^3$ is a hydrogen atom, at least two of R$^{1a}$, R$^{1b}$, R$^{2a}$, and R$^{2b}$ each is independently a halogen atom; a primary, secondary, or tertiary alkyl group having from one to eight carbon atoms; or a primary, secondary, or tertiary alkyl group having two to eight carbon atoms and at least one ether linkage; or, at least one of R$^{1a}$, R$^{1b}$, R$^{2a}$, and R$^{2b}$ is a primary, secondary, or tertiary alkyl group having two to eight carbon atoms and at least one ether linkage; and wherein, when R$^3$ is a primary alkyl group having one to eight carbon atoms, at least one of R$^{1a}$, R$^{1b}$, R$^{2a}$, and R$^{2b}$ is a halogen atom; a primary, secondary, or tertiary alkyl group having from one to eight carbon atoms; or a primary, secondary, or tertiary alkyl group having two to eight carbon atoms and at least one ether linkage; and wherein, when at least two of R$^{2a}$, R$^{2b}$, and R$^3$ are tertiary alkyl groups, the tertiary alkyl groups are non-adjacent.

2. The compound of claim 1, wherein the primary, secondary, or tertiary alkyl groups having one to eight carbon atoms have from one to four carbon atoms.

3. The compound of claim 1, wherein the primary, secondary, or tertiary alkyl groups having two to eight carbon atoms and at least one ether linkage have two to five carbon atoms and one or two ether linkages.

4. The compound of claim 1, wherein $R^3$ is a tertiary alkyl group.

5. The compound of claim 4, wherein the tertiary group is tert-butyl group.

6. The compound of claim 1, wherein the compound is selected from the group consisting of 2,6-dimethyl-4-tert-butylphenylsulfur trifluoride; 2,6-dimethyl-3-chloro-4-tert-butylphenylsulfur trifluoride; 2,6-dimethyl-3,5-dichloro-4-tert-butylphenylsulfur trifluoride; 4-tert-butylphenylsulfur trifluoride; 2,4,6-trimethylphenylsulfur trifluoride; 2,4-dimethylphenylsulfur trifluoride; 2,5-dimethylphenylsulfur trifluoride; 2,6-dimethylphenylsulfur trifluoride; 4-fluorophenylsulfur trifluoride; 4-chlorophenylsulfur trifluoride; 3-methyl-4-chlorophenylsulfur trifluoride; 2,4,6-tri(isopropyl)phenylsulfur trifluoride; 2,6-bis(methoxymethyl)phenylsulfur trifluoride; 2,6-bis(methoxymethyl)-4-tert-butylphenylsulfur trifluoride; 2,6-bis(ethoxymethyl)-4-tert-butylphenylsulfur trifluoride; 2,6-bis(isopropoxymethyl)-4-tert-butylphenylsulfur trifluoride; 2,6-bis(isobutoxymethyl)-4-tert-butylphenylsulfur trifluoride; and 2,6-bis(tert-butoxymethyl)-4-tert-butylphenylsulfur trifluoride.

7. The compound of claim 1, wherein the compound is selected from the group consisting of 2,6-dimethyl-4-tert-butylphenylsulfur trifluoride; 2,6-dimethyl-3-chloro-4-tert-butylphenylsulfur trifluoride; 2,6-dimethyl-3,5-dichloro-4-tert-butylphenylsulfur trifluoride; 2,6-bis(methoxymethyl)phenylsulfur trifluoride; 2,6-bis (methoxymethyl)-4-tert-butylphenylsulfur trifluoride; 2,6-bis(ethoxymethyl)-4-tert-butylphenylsulfur trifluoride; 2,6-bis(isopropoxymethyl)-4-tert-butylphenylsulfur trifluoride; and 2,6-bis (isobutoxymethyl)-4-tert-butylphenylsulfur trifluoride.

8. A compound according to formula (Ia):

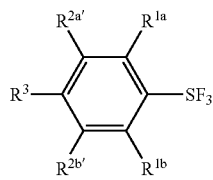

in which:
- $R^{1a}$ and $R^{1b}$ are independently a hydrogen atom; a primary or secondary alkyl group having from one to eight carbon atoms; or a primary, secondary, or tertiary alkyl group having two to eight carbon atoms and at least one ether linkage;
- $R^{2a'}$ and $R^{2b'}$ are independently a hydrogen atom or a halogen atom; and
- $R^3$ is a hydrogen atom; a halogen atom; a primary, secondary, or tertiary alkyl group having from one to eight carbon atoms; or a primary, secondary, or tertiary alkyl group having two to eight carbon atoms and at least one ether linkage;
- wherein when $R^3$ is a hydrogen atom, $R^{1a}$ and $R^{1b}$ are independently a primary or secondary alkyl group having from one to eight carbon atoms or at least one of $R^{1a}$ and $R^{1b}$ is a primary, secondary, or tertiary alkyl group having two to eight carbon atoms and at least one ether linkage, and
- wherein, when $R^3$ is a primary alkyl group having one to eight carbon atoms, at least one of $R^{1a}$ and $R^{1b}$ is a primary or secondary alkyl group having from one to eight carbon atoms or a primary, secondary, or tertiary alkyl group having two to eight carbon atoms and at least one ether linkage.

9. The compound of claim 8, wherein the primary, secondary, or tertiary alkyl groups having one to eight carbon atoms have from one to four carbon atoms.

10. The compound of claim 8, wherein the alkyl groups having two to eight carbon atoms and at least one ether linkage have two to five carbon atoms and one or two ether linkages.

11. The compound of claim 10, wherein the alkyl group is selected from the group consisting of $CH_2OCH_3$, $CH_2OCH_2CH_3$, $CH_2OCH_2CH_2CH_3$, $CH_2OCH(CH_3)_2$, $CH_2OCH_2(CH_2)_2CH_3$, $CH_2OCH(CH_3)CH_2CH_3$, $CH_2OCH_2CH(CH_3)_2$, $CH_2OC(CH_3)_3$, $CH_2OCH_2C(CH_3)_3$, $CH_2OCH_2CH_2OCH_3$, $CH_2OCH_2CH_2CH_2OCH_3$, $CH_2OCH_2CH_2OCH_2CH_3$, $CH_2CH_2OCH_3$, $CH_2CH_2OCH_2CH_3$, $CH_2CH_2OCH(CH_3)_2$, $CH_2CH_2OCH_2CH_2OCH_3$, $CH(CH_3)OCH_3$, $CH(CH_3)OCH_2CH_3$, $C(CH_3)_2OCH_3$, and $C(CH_3)_2OCH_2CH_3$.

12. The compound of claim 11, wherein the alkyl group is selected from the group consisting of $CH_2OCH_3$, $CH_2OCH_2CH_3$, $CH_2OCH(CH_3)_2$, and $CH_2OCH_2CH(CH_3)_2$.

13. The compound of claim 8, wherein $R^3$ is a tertiary alkyl group.

14. The compound of claim 13, wherein the tertiary group is tert-butyl group.

15. A compound according to formula (II):

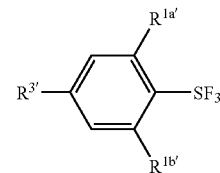

in which:
- $R^{1a'}$ and $R^{1b'}$ are independently a hydrogen atom or a primary or secondary alkyl group having from one to eight carbon atoms; and
- $R^{3'}$ is a hydrogen atom, a halogen atom, or a primary, secondary, or tertiary alkyl group having from one to eight carbon atoms;
- wherein when $R^{3'}$ is a hydrogen atom, $R^{1a'}$ and $R^{1b'}$ are independently a primary or secondary alkyl group having from one to eight carbon atoms, and wherein, when $R^{3'}$ is a primary alkyl group having one to eight carbon atoms, at least one of $R^{1a'}$ and $R^{1b'}$ is a primary or secondary alkyl group having from one to eight carbon atoms.

16. The compound of claim 15, wherein the primary, secondary, or tertiary alkyl groups have from one to four carbon atoms.

17. The compound of claim 15, wherein $R^{3'}$ is a tertiary alkyl group.

18. The compound of claim 17, wherein the tertiary group is tert-butyl group.

19. A compound according to formula (Ib):

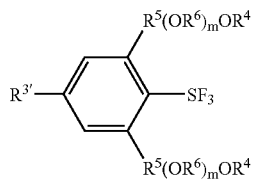

in which
R$^{3'}$ is a hydrogen atom, a halogen atom, or a primary, secondary, or tertiary alkyl group having from one to eight carbon atoms; and
R$^4$ is a primary, secondary, or tertiary alkyl group; and
R$^5$ and R$^6$ are independently an alkylene group; the number of total carbon atoms of R$^4$, R$^5$, and R$^6$ is eight or less, and m is 0 or 1.

20. The compound of claim 19, wherein the primary, secondary, or tertiary alkyl groups have four carbon atoms or less.

21. The compound of claim 19, wherein R$^{3'}$ is a hydrogen atom or a tertiary alkyl group.

22. The compound of claim 21, wherein the tertiary group is tert-butyl group.

23. The compound of claim 19, wherein R$^4$ is a primary or secondary alkyl group.

24. The compound of claim 19, wherein m is 0.

25. The compound of claim 19, wherein R$^5$ is methylene group.

26. A method of introducing one or more fluorine atoms into a target compound comprising:
contacting a fluorinating agent of formula (I) from claim 1 with the target compound under conditions that allow one or more fluorine atoms to be introduced into the target compound.

27. The method of claim 26, wherein the target compound has one or more oxygen or oxygen-containing groups which are replaced by the introduction of the one or more fluorine atoms.

28. The method of claim 26, wherein the target compound has one or more sulfur or sulfur-containing groups which are replaced by the introduction of the one or more fluorine atoms.

29. The method of claim 26, wherein the fluorinating agent is selected from the group consisting of 2,6-dimethyl-4-tert-butylphenylsulfur trifluoride; 2,6-dimethyl-3-chloro-4-tert-butylphenylsulfur trifluoride; 2,6-dimethyl-3,5-dichloro-4-tert-butylphenylsulfur trifluoride; 4-tert-butylphenylsulfur trifluoride; 2,4,6-trimethylphenylsulfur trifluoride; 2,4-dimethylphenylsulfur trifluoride; 2,5-dimethylphenylsulfur trifluoride; 2,6-dimethylphenylsulfur trifluoride; 4-fluorophenylsulfur trifluoride; 4-chlorophenylsulfur trifluoride; 3-methyl-4-chlorophenylsulfur trifluoride; 2,4,6-tri(isopropyl)phenylsulfur trifluoride; 2,6-bis(methoxymethyl)phenylsulfur trifluoride; 2,6-bis(methoxymethyl)-4-tert-butylphenylsulfur trifluoride; 2,6-bis(ethoxymethyl)-4-tert-butylphenylsulfur trifluoride; 2,6-bis(isopropoxymethyl)-4-tert-butylphenylsulfur trifluoride; 2,6-bis(isobutoxymethyl)-4-tert-butylphenylsulfur trifluoride; and 2,6-bis(tert-butoxymethyl)-4-tert-butylphenylsulfur trifluoride.

30. The method of claim 26, wherein the fluorinating agent is selected from the group consisting of 2,6-dimethyl-4-tert-butylphenylsulfur trifluoride; 2,6-dimethyl-3-chloro-4-tert-butylphenylsulfur trifluoride; 2,6-dimethyl-3,5-dichloro-4-tert-butylphenylsulfur trifluoride; 2,6-bis(methoxymethyl)phenylsulfur trifluoride; 2,6-bis(methoxymethyl)-4-tert-butylphenylsulfur trifluoride; 2,6-bis(ethoxymethyl)-4-tert-butylphenylsulfur trifluoride; 2,6-bis(isopropoxymethyl)-4-tert-butylphenylsulfur trifluoride; and 2,6-bis(isobutoxymethyl)-4-tert-butylphenylsulfur trifluoride.

31. A method of introducing one or more fluorine atoms into a target compound comprising:
contacting a fluorinating agent of formula (Ia) from claim 8 with the target compound under conditions that allow one or more fluorine atoms to be introduced into the target compound.

32. The method of claim 31, wherein the target compound has one or more oxygen or oxygen-containing groups which are replaced by the introduction of the one or more fluorine atoms.

33. The method of claim 31, wherein the target compound has one or more sulfur or sulfur-containing groups which are replaced by the introduction of the one or more fluorine atoms.

34. A method of introducing one or more fluorine atoms into a target compound comprising:
contacting a fluorinating agent of formula (II) from claim 15 with the target compound under conditions that allow one or more fluorine atoms to be introduced into the target compound.

35. The method of claim 34, wherein the target compound has one or more oxygen or oxygen-containing groups which are replaced by the introduction of the one or more fluorine atoms.

36. The method of claim 34, wherein the target compound has one or more sulfur or sulfur-containing groups which are replaced by the introduction of the one or more fluorine atoms.

37. A method of introducing one or more fluorine atoms into a target compound comprising:
contacting a fluorinating agent of formula (Ib) from claim 19 with the target compound under conditions that allow one or more fluorine atoms to be introduced into the target compound.

38. The method of claim 37, wherein the target compound has one or more oxygen or oxygen-containing groups which are replaced by the introduction of the one or more fluorine atoms.

39. The method of claim 37, wherein the target compound has one or more sulfur or sulfur-containing groups which are replaced by the introduction of the one or more fluorine atoms.

* * * * *

UNITED STATES PATENT AND TRADEMARK OFFICE
CERTIFICATE OF CORRECTION

PATENT NO. : 7,381,846 B2
APPLICATION NO. : 11/828162
DATED : June 3, 2008
INVENTOR(S) : Teruo Umemoto and Rajendra P. Singh It is certified that error appears in the above-identified patent and that said Letters Patent is hereby corrected as shown below:

Columns 53 and 54, Table 5, Ex. 55a, the entry chemical structure column should be corrected to read "PhOCF$_3$".

Signed and Sealed this

Twenty-fourth Day of February, 2009

JOHN DOLL
*Acting Director of the United States Patent and Trademark Office*